US006914148B2

(12) United States Patent
Manoharan et al.

(10) Patent No.: US 6,914,148 B2
(45) Date of Patent: Jul. 5, 2005

(54) GUANIDINIUM FUNCTIONALIZED INTERMEDIATES

(75) Inventors: Muthiah Manoharan, Carlsbad, CA (US); Phillip Dan Cook, Fallbrook, CA (US); Thazha P. Prakash, Carlsbad, CA (US); Venkatraman Mohan, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 475 days.

(21) Appl. No.: 10/247,893

(22) Filed: Sep. 20, 2002

(65) Prior Publication Data

US 2003/0092046 A1 May 15, 2003

Related U.S. Application Data

(60) Division of application No. 09/612,531, filed on Jul. 7, 2000, now Pat. No. 6,534,639, which is a continuation-in-part of application No. 09/349,040, filed on Jul. 7, 1999, now Pat. No. 6,593,466.

(51) Int. Cl.$^7$ .................................................. C07F 9/02

(52) U.S. Cl. ....................... 558/70; 536/23.1; 536/24.3; 536/24.5; 536/26.7; 536/26.8

(58) Field of Search ......................... 536/23.1, 24.3, 536/24.5, 26.7, 26.8; 558/70

(56) References Cited

U.S. PATENT DOCUMENTS

| | | | |
|---|---|---|---|
| 2,933,502 A | 4/1960 | Klopping | |
| 3,687,808 A | 8/1972 | Merigan et al. | |
| 3,812,173 A | 5/1974 | Giraudon | |
| 3,896,160 A | 7/1975 | Gaetzi | |
| 3,929,821 A | 12/1975 | Beard et al. | |
| 3,929,823 A | 12/1975 | Beard et al. | |
| 3,929,824 A | 12/1975 | Beard et al. | |
| 3,950,395 A | 4/1976 | Kolling et al. | |
| 3,965,113 A | 6/1976 | Beard et al. | |
| 3,993,682 A | 11/1976 | Kolling et al. | |
| 4,024,176 A | 5/1977 | Kolling et al. | |
| 4,032,655 A | 6/1977 | Kolling et al. | |
| 4,415,732 A | 11/1983 | Caruthers et al. | |
| 4,458,066 A | 7/1984 | Caruthers et al. | |
| 4,469,863 A | 9/1984 | Ts'o et al. | |
| 4,476,301 A | 10/1984 | Imbach et al. | |
| 4,500,707 A | 2/1985 | Caruthers et al. | |
| 4,668,777 A | 5/1987 | Caruthers et al. | |
| 4,725,677 A | 2/1988 | Köster et al. | |
| 4,794,174 A | 12/1988 | Secrist, III | |
| 4,973,679 A | 11/1990 | Caruthers et al. | |
| 4,977,189 A | 12/1990 | Tomcufcik et al. | 514/603 |
| 5,023,243 A | 6/1991 | Tullis | 514/44 |
| 5,034,506 A | 7/1991 | Summerton et al. | 528/391 |
| 5,132,418 A | 7/1992 | Caruthers et al. | |
| RE34,069 | 9/1992 | Köster et al. | |
| 5,166,315 A | 11/1992 | Summerton et al. | 528/406 |
| 5,177,196 A | 1/1993 | Meyer, Jr. et al. | 536/22.1 |
| 5,185,444 A | 2/1993 | Summerton et al. | 544/81 |
| 5,188,897 A | 2/1993 | Suhadolnik et al. | 428/402.2 |
| 5,210,264 A | 5/1993 | Yau | 558/167 |
| 5,214,134 A | 5/1993 | Weis et al. | 536/25.3 |
| 5,216,141 A | 6/1993 | Benner | 536/27.13 |
| 5,235,033 A | 8/1993 | Summerton et al. | 528/391 |
| 5,264,423 A | 11/1993 | Cohen et al. | 514/44 |
| 5,264,562 A | 11/1993 | Matteucci | 536/23.1 |
| 5,264,564 A | 11/1993 | Matteucci | 536/23.1 |
| 5,276,019 A | 1/1994 | Cohen et al. | 514/44 |
| 5,278,302 A | 1/1994 | Caruthers et al. | 536/24.5 |
| 5,286,717 A | 2/1994 | Cohen et al. | 514/44 |
| 5,321,131 A | 6/1994 | Agrawal et al. | 536/25.34 |
| 5,399,676 A | 3/1995 | Froehler | 536/23.1 |
| 5,405,938 A | 4/1995 | Summerton et al. | 528/406 |
| 5,405,939 A | 4/1995 | Suhadolnik et al. | 530/322 |
| 5,434,257 A | 7/1995 | Matteucci et al. | 536/24.3 |
| 5,453,496 A | 9/1995 | Caruthers et al. | 536/24.5 |
| 5,455,233 A | 10/1995 | Spielvogel et al. | 514/44 |
| 5,466,677 A | 11/1995 | Baxter et al. | 514/44 |
| 5,470,967 A | 11/1995 | Huie et al. | 536/24.3 |

(Continued)

FOREIGN PATENT DOCUMENTS

| | | |
|---|---|---|
| CH | 612 925 | 8/1979 |
| CH | 615 157 | 1/1980 |
| DE | 2 117 293 | 10/1971 |
| DE | 2 147 103 | 3/1972 |
| DE | 2 109 454 | 9/1972 |
| DE | 2 250 911 | 4/1974 |
| DE | 33 28 502 | 2/1985 |
| EP | 0 071 926 A1 * | 2/1983 |
| EP | 0 850 950 | 7/1998 |
| FR | 2.086.795 | 12/1971 |
| JP | 48-80560 | 10/1972 |
| JP | 10-81686 | 3/1998 |
| WO | WO 99/14226 | 3/1999 |

OTHER PUBLICATIONS

R. W. Hoffman, "Reactions of Electron–Rich Olefins," *Angewandte Chemie, International Edition*, 7(10), 754–765 (Oct., 1968).*

N. Wiberg, "Tetraaminoethylenes as Strong Electron Donors," *Angewandte Chemie, International Edition*, 7(10), 766–778 (Oct., 1968).*

Leyh et al., "Structures of Manganese(II) Complexes with ATP, ADP, and Phosphocreatine in the Reactive Central Complexes with Creatine Kinase: Electron Paramagnetic Resonance Studies with Oxygen–17–Labeled Ligands," *Biochemistry*, 24(2), 308–316 (Jan. 15, 1985).*

(Continued)

*Primary Examiner*—James O. Wilson
*Assistant Examiner*—L. E. Crane
(74) *Attorney, Agent, or Firm*—Woodcock Washburn LLP

(57) ABSTRACT

The present invention provides oligomers which are specifically hybridizable with a selected sequence of RNA or DNA wherein at least one of the nucleoside moieties of the oligomer is modified to include a guanidinium group. These oligomers are useful for diagnostic, therapeutic and investigative purposes.

5 Claims, 22 Drawing Sheets

U.S. PATENT DOCUMENTS

| | | | | |
|---|---|---|---|---|
| 5,476,925 | A | 12/1995 | Letsinger et al. | 536/23.1 |
| 5,489,677 | A | 2/1996 | Sanghvi et al. | 536/22.1 |
| 5,519,126 | A | 5/1996 | Hecht | 536/24.3 |
| 5,536,821 | A | 7/1996 | Agrawal et al. | 536/22.1 |
| 5,539,082 | A | 7/1996 | Nielsen et al. | 530/300 |
| 5,541,306 | A | 7/1996 | Agrawal et al. | 536/22.1 |
| 5,541,307 | A | 7/1996 | Cook et al. | 536/23.1 |
| 5,550,111 | A | 8/1996 | Suhadolnik et al. | 514/44 |
| 5,561,225 | A | 10/1996 | Maddry et al. | 536/23.1 |
| 5,563,253 | A | 10/1996 | Agrawal et al. | 536/22.1 |
| 5,571,799 | A | 11/1996 | Tkachuk et al. | 514/47 |
| 5,587,361 | A | 12/1996 | Cook et al. | 514/44 |
| 5,596,086 | A | 1/1997 | Matteucci et al. | 536/22.1 |
| 5,602,240 | A | 2/1997 | De Mesmaeker et al. | 536/23.1 |
| 5,608,046 | A | 3/1997 | Cook et al. | 536/23.1 |
| 5,610,289 | A | 3/1997 | Cook et al. | 536/25.34 |
| 5,618,704 | A | 4/1997 | Sanghvi et al. | 435/91.5 |
| 5,623,070 | A | 4/1997 | Cook et al. | 536/27.6 |
| 5,625,050 | A | 4/1997 | Beaton et al. | 536/24.1 |
| 5,633,360 | A | 5/1997 | Bischofberger et al. | 536/22.1 |
| 5,663,312 | A | 9/1997 | Chaturvedula | 536/22.1 |
| 5,670,633 | A | 9/1997 | Cook et al. | 536/23.1 |
| 5,677,437 | A | 10/1997 | Teng et al. | 536/23.1 |
| 5,677,439 | A | 10/1997 | Weis et al. | 536/23.1 |
| 5,714,331 | A | 2/1998 | Buchardt et al. | 435/6 |
| 5,719,262 | A | 2/1998 | Buchardt et al. | 530/300 |
| 5,760,202 | A | 6/1998 | Cook et al. | 536/22.1 |
| 6,166,197 | A * | 12/2000 | Cook et al. | 536/24.5 |
| 6,271,358 | B1 * | 8/2001 | Manoharan et al. | 536/23.1 |
| 6,534,639 | B1 * | 3/2003 | Manoharan et al. | 536/23.1 |

OTHER PUBLICATIONS

Ramasamy et al., "Nucleoside Peptides—IX. Synthesis of Peptide Derivatives of Sangivamycic Acid and Deaminosangivamycic Acid," *Tetrahedron*, 44(4), 1023–1034 (1988).*

Harusawa et al., "Efficient and β–Stereoselective Synthesis of 4(5)–methyl–5(4)–(5–amino–5–deoxy–β–D– ribofuranosyl)imidazole and Related Compounds Exhibiting Antiulcer Activity," *Chemical & Pharmaceutical Bulletin*, 45(1), 53–61 (Jan., 1997); *Chemical Abstracts*, 126(15), p. 596, Abstr. No. 199776f (Apr. 14, 1997).*

Barawkar et al. (I), "Deoxynucleic Guanidines/PNA (DNG/PNA) Chimeras Oligonucleoside Analogue Containing Cationic Guanidinium and Neutral Amide Linkages," *J. American Chemical Society*, 121(44), 10418–10419 (Nov. 10, 1999).*

Barawkar et al. (II), "Synthesis, Biophysical Properties, and Nuclease Resistance Properties of Mixed Backbone Oligodeoxynucleotides Containing Cationic Internucleoside Guanidinium Linkages: Deoxynucleic Guanidine/DNA Chimeras," *Proc. National Academy of Sciences USA*, 95(19), 11047–11052 (Sep., 1998).*

Barawkar et al. (III), "Synthesis of Protected Guanidinium Linked Dinucleoside for Incorporable into an Oligonucleotide Using a Solid Phase DNA Methodology," *Bioorganic & Medicinal Chemistry Letters*, 8(12), 1517–1520 (1998).*

Doronina et al., Synthesis of 5–Guanidinopyrimidine Nucleosides for Triple Helix–Mediated Guanine and Cytosine Recognition, *Tetrahedron Letters*, 39(7), 547–550 (Feb. 12, 1998).*

Pannecouque et al. (I), "Synthesis, Enzymatic Stability and Physicochemical Properties of Oligonucleotides Containing an N–Cyanoguanidine Linkage," *Tetrahedron*, 50(24), 7231–7246 (Jun. 13, 1994).*

Pannecouque et al. (II), "Mixed Oligonucleotide Analogs with an Acyclic Carbohydrate Moiety and N–Cyanoguanidine Functionality," *Bioorganic & Medicinal Chemistry Letters*, 4(10), 1203–1206 (May 19, 1994).*

Vandendriessche et al., "Synthesis, Enzymatic Stability and Base Pairing Properties of Oligothymidylates Containing Thymidine Dimers with Different N–Substituted Guanidine Linkages," *J. Chemical Society, Perkin Transactions 1: Organic and Bio–organic Chemistry, 1993*, (Issue No. 14), 1567–1575 (Jul. 21, 1993).*

Pannecouque et al. (III), "Dimeric Building Blocks with N–Cyanoguanidine Linkage for Oligonucleotide Synthesis," *Tetrahedron Letters*, 33(49), 7609–7612 (Dec. 1, 1992).*

Agrawal et al. (eds.), "Methods of Molecular Biology", in *Protocols for Oligonucleotide Conjugates*, Agrawal, S. (ed.), Humana Press, New Jersey, 1994, vol. 26, 1–72.

Altmann, K. et al., "Second Generation of Antisense Oligonucleotides: From Nuclease Resistance to Biological Efficacy in Animals," *Chimia*, 1996, 50, 168–176 (Apr., 1996.

Altmann, K. et al., "Second Generation Antisense Oligonucleotides–Inhibition of Pkc–1 and c–RAF Kinase Expression by Chimeric Oligonucleotides Incorporating 6–Substituted Carbocyclic Nucleosides and 2'–O–Ethylene Glycol Substituted Ribonucleosides," *Nucleosides & Nucleotides*, 1997, 16(7–9), 917–926.

Altmann, K. et al., "Second–Generation Antisense Oligonucleotides: Structure–Activity Relationships and the Design of Improved Signal–Transduction Inhibitors", *Biochem. Soc. Trans.*, 1996, 24, 630–637.

Alu1, R.H. et al., "Oxalyl–CPG: a labile support for synthesis of sensitive oligonucleotide derivatives", *Nucl. Acid Res.*, 1991, 19, 1527–1532.

Baker, B.F. et al., "2'–O–(2–Methoxy)ethyl–modified Anti–intercellular Adhesion Molecule 1 (ICAM–1) Oligonucleotides Selectively Increase the ICAM–1 Translation Initiation Complex in Human Umbilical Vein Endothelial Cells", *J. Biol. Chem.*, 1997, 272, 11994–12000 (May 2, 1997).

Beal, P. A. et al., "Second Structural Motif for Recognition of DNA by Oligonucleotide–Directed Triple–Helix Formation," *Science*, 1991, 251, 1360–1363 (Mar. 15, 1991).

Beaucage, S.L. et al., "Advances in the Synthesis of Oligonucleotides by the Phosphoramidite Approach", *Tetrahedron*, 1992, 48, 2223–2311.

Behrens et al., "A New Achiral Reagent for the Incorporation of Multiple Amino Groups into Oligonucleotides," *Bioorg. Med. Chem. Lett.*, 1995, 5(16), 1785–1790.

Bock, L. C. et al., "Selection of Single–Stranded DNA Molecules that Bind and Inhibit Human Thrombin," *Nature*, 1992, 355, 564–566 (Feb. 6, 1992).

Conte, M. R., "Confirmational Properties and Thermodynamics of the RNA Duplex r(CGCAAAUUUGCG)2: Comparison with the DNA Analogue d(CGCAAATTTGCG)2," *Nucl. Acids Res.*, 1997, 25(13), 2627–2634.

Cook, P.D., "Medicinal Chemistry of Antisense Oligonucleotides—future opportunities", *Anti–Cancer Drug Design*, 1991, 6, 585–607.

Crooke, S. T., "Progress in Antisense Therapeutics," *Medicinal Research Reviews*, 1996, 16(4), 319–344.

Cuenourd et al., "Dual Recognition of Double–Stranded DNA by 2'–Aminoethoxy–Modified Oligonucleotides," *Angew. Chem. Int. Ed.*, 1998, 37(9), 1288–1291.

Delgado, C. et al., "The Uses and Properties of PEG–Linked Proteins", *Crit. Rev. in Therapeutic Drug Carrier Sys.*, 1992, 9, 249–304.

De Mesmaeker, A. et al., "Antisense Oligonucleotides", *Acc. Chem. Res.*, 1995, 28, 366–374.

Derocque et al., "Composés organiques sulfurés. XXII.— Diaryl–2,5 trithia–1,6,6aS$^{IV}$ diaza–3,4 pentalénes," *Bull. De la Société Chimique de France*, 1968, 5, 2062–2066 (English abstract provided).

Egli, M. et al., "RNA Hydration: A Detailed Look," *Biochemistry*, 1996, 35, 8489–8494.

Englisch, U. et al., "Chemically Modified Oligonucleotides as Probes and Inhibitors", *Angew. Chem. Int. Ed. Eng.*, 1991, 30, 613–629 (Jun., 1991).

Escudé, C. et al., "Stability of triple helices containing RNA and DNA strands: experimental and molecular modeling studies," *Nucl. Acids Res.*, 1993, 21(24), 5547–5553.

Fedoroff, O. Y. et al., "Structure of a DNA: RNA Hybrid Duplex Why Rnase H Does Not Cleave Pure RNA," *J. Mol. Biol.*, 1993, 233, 509–523.

Freier, S.M. et al., "The ups and downs of nucleic acid duplex stability: structure–stability studies on chemically–modified DNA:RNA duplexes", *Nucl. Acids Res.*, 1997, 25, 4429–4443.

Giovannangeli et al., "Progress in Developments of Triplex–Based Strategies," *Antisense Nucl. Acid Drug Dev.*, 1997, 7, 413–421.

Gonzalez, C. et al., "Structure and Dynamics of a DNA–RNA Hybrid Duplex with a Chral Phosphorothioate Moiety: NMR and Molecular Dynamics with Conventional and Time–Averaged Restraints," *Biochemistry*, 1995, 34, 4969–4982.

Griffin, L. C. et al., "In Vivo Anticoagulant Properties of a Novel Nucleotide–Based Thrombin Inhibitor and Demonstration of Regional Anticoagulation in Extracorporeal Circuits," *Blood*, 1993, 81, 3271–3276 (Jun. 15, 1993).

Hamm, M. L. et al., "Incorporation of 2'–Deoxy–2'–mercaptocytidine into Oligonucleotides via Phosphoramidite Chemistry," *J. Org. Chem.*, 1997, 62, 3415–3420.

Horton, N. C. et al., "The Structure of an RNA/DNA Hybrid: A Substrate of the Ribonuclease Activity of HIV–1 Reverse Transcriptase," *J. Mol. Biol.*, 1996, 264, 521–533.

Krolikiewicz, K. et al., "The Synthesis of 2–Fluoropurine Nucleosides", *Nucleosides & Nucleotides*, 1994, 13, 673–678.

Kroshwitz, J.I., "Polynucleotides", *Concise Encyclopedia of Polymer Science and Engineering*, 1990, John Wiley & Sons, New York, 858–859.

Kung et al., "One–Flask Synthesis of 6–Thioguanosine and 2'–Deoxy–6–Thioguanosine," *Tetra Lett.*, 1991, 32(32), 3919–3922.

Lane, A. N. et al., "NMR Assignments and Solution Conformation of the DNA–RNA Hybrid Duplex d(GTGAACT-T)–r(AAGUUCAC)," *Eur. J. Biochem.*, 1993, 215, 297–306.

Lesnik, E. A. et al., "Relative Thermodynamic Stability of DNA, RNA, and DNA: RNA Hybrid Duplexes: Relationship with Base Composition and Structure," *Biochemistry*, 1995, 34(34), 10807–10815.

Maher, "Prospects for the Therapeutic Use of Antigene Oligonucleotides," *Cancer Invest.*, 1996, 14(1), 66–82.

Martin, P., "Ein neuer Zugang zu 2'–O–Alkylribonucleosiden und Eigenschaften deren Oligonucleotide", *Helvetica Chemica Acta*, 1995, 78, 486–504 (English summary included).

Miller, P.S. et al., "A New approach to chemotherapy based on molecular biology and nucleic acid chemistry: Matagen (masking tape for gene expression)", *Anti–Cancer Drug Des.*, 1987, 2, 117–128.

Milligan, J. F. et al., "Current Concepts in Antisense Drug Design," *Journal of Medicinal Chemistry*, 1993, 36(14), 1923–1937 (Jul. 9, 1993).

Neidel, "Recent developments in triple–helix regulation of gene expression," *Anti–Cancer Drug Des.*, 1997, 12, 433–442.

Nielsen, P.E. et al., "Sequence–Selective Recognition of DNA by Strand Displacement with a Thymine–Substituted Polyamide", *Science*, 1991, 254, 1497–1500(Dec. 6, 1991).

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Polushin, N. N. et al., "Synthesis of Oligonucleotides Containing 2'–Azido–and 2'–Amino–2'–deoxyuridine Using Phosphotriester Chemistry," *Tetrahedron Letts.*, 1996, 37(19), 3227–3230.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333 (Jun. 21, 1991).

Searle, M. S. et al., "On the Stability of Nucleic Acid Structures in Solution: Enthalpy–Entropy Compensations, Internal Rotations and Reversibility," *Nucl. Acids Res.*, 1993, 21(9), 2051–2056.

Stein, C.A. et al., "Oligodeoxynucleotides as Inhibitors of Gene Expression: A Review", *Cancer Res.*, 1988, 48, 2659–2668 (May, 1988).

Thomson, J. B. et al., "Synthesis and Properties of Diuridine Phosphate Analogues Containing Thio and Amino Modifications," *J. Org. Chem.*, 1996, 61, 6273–6281.

Uhlmann, E. et al., "Antisense Oligonucleotides: A New Therapeutic Principle", *Chem. Reviews*, 1990, 90, 544–584 (May, 1990).

Wagner, R. W. et al., "Antisense Gene Inhibition by Oligonucleotides Containing C–5 Propyne Pyrimidines," *Science*, 1993, 260, 1510–1513 (Jun. 4, 1993).

Wright, P. et al., "Large Scale Synthesis of Oligonucleotides via phosphoramidite Nucleosides and a High–loaded Polystyrene Support", *Tetrahedron Letts.*, 1993, 34, 3373–3376.

Young, S. L. et al., "Triple Helix Formation Inhibits Transcription Elongation In Vitro," *Proc. Natl. Acad. Sci. USA*, 1991, 88, 10023–10026 (Nov., 1991).

Cuenoud, B., et al., "Dual recognition of double–stranded DNA by 2'–aminoethoxy–modified oligonucleotides" *Angew. Chem. Int. Ed.*, 1998, 37(9), 1288–1291.

Escudé, C., et al., "Stability of triple helices containing RNA and DNA strands: experimental and molecular studies," *Nucleic Acid Res.*, 1993, 21(24), 5547–5553.

Koshkin, A.A., et al., "LNA (locked nucleic acids): synthesis of the adenine, cytosine, guanine, 5–methylcytosine, thymiine and uracil bicyclonucleoside monomers, oligomerisation, and unprecedented nucleic acid recognition," *Tetrahedron*, 1998, 54, 3607–3630.

Koshkin, A.A., et al., "LNA (locked nucleic acid): an RNA mimic forming exceedingly stable LNA:LNA duplexes," *J. Am. Chem. Soc.*, 1998, *120*, 13252–13253 (Web Pub Dec. 8, 1998).

Kumar, R., et al., "The first analogues of LNA (locked nucleic acids): phosphorothioate–LNA and 2'–thio–LNA," *Bioorg. Med. Chem. Lett.*, 1998, *8*, 2219–2222.

Migawa, M.T., et al., "A two step synthesis of the nucleoside Q precursor 2–amino–5–cyanopyrrolo[2,3–d] pyrimidin–4–one (PreQo)," *Synthetic Communications*, 1996, *26(17)*, 3317–3322.

Petersen, M., et al., "The conformations of locked nucleic acids (LNA)," *J. Mol. Recognit.*, 2000, *13*, 44–53.

Porcari, A.R., et al., "Total synthesis of the naturally occurring antibiotic toyocamycin using new and improved synthetic procedures," *Nucleosides and Nucleotides*, 1999, *18(2)*, 153–159.

Ramasamy, K., et al., "Total and stereospecific synthesis of cadeguomycin, 2'–deoxycadeguomycin, *ara*–cadeguomycin, and certain related nucleosides," *J. Chem. Soc. Perkin Trans., I*, 1989, 2375–2384.

Singh, S.K., et al., "LNA (locked nucleic acids): synthesis and high–affinity nucleic acid recognition," *Chem. Commun.*, 1998, *4*, 455–456.

Singh, S.K., et al., "Synthesis of 2'–amino–LNA: a novel conformationally restricted high–affinity oligonucleotide analogue with a handle," *J. Org. Chem.*, 1998, *63*, 10035–10039.

Thomson, J.B., "Synthesis and properties of diuridine phosphate analogues containing thio and amino modifications," *J. Org. Chem.*, 1996, *61*, 6273–6281.

Wahlestedt, C., et al., "Potent and nontoxic antisense oligonucleotides containing locked nucleic acids," *Proc. Natl. Acad. Sci. U.S.A.*, 2000, *97(10)*, 5633–5638(Nov. 9, 2000).

Wengel, J., et al., "LNA (locked nucleic acid)," *Nucleosides, Nucleotides*, 1999, *18(6 & 7)*, 1365–1370.

* cited by examiner

2'-O-(2-Guanidinium-ethyl): Supercationic Modification $\Delta$Tm=3.0°C (dispersed) 0.6°C (placed together) as a diester (Relative to 2'-deoxy P=S)

Entropy effect due to rigidity; Weak Gauche Effect

Very high nuclease resistance due to charge effect

Charge delocalization over four atoms

5

6

7

8  R = CE
10 R = Ph
12 R = t-Bu

9  R = CE
11 R = Ph
13 R = t-Bu

R = TBDPS

GUANIDINIUM FUNCTIONALIZED INTERMEDIATES

RELATED APPLICATION DATA

This patent application is a divisional application of application Ser. No. 09/612,531, filed Jul. 7, 2000, now U.S. Pat. No. 6,539,639, which is a continuation-in-part of application Ser. No. 09/349,040, filed Jul. 7, 1999, now U.S. Pat. No. 6,593,466, the contents of which are incorporated herein by reference.

FIELD OF THE INVENTION

The present invention relates to monomers and oligomers containing guanidinium moieties and methods of preparing such oligomers. The oligomers of the present invention are used for investigative and therapeutic purposes.

BACKGROUND OF THE INVENTION

It is well known that most of the bodily states in mammals, including most disease states, are affected by proteins. Classical therapeutic modes have generally focused on interactions with such proteins in an effort to moderate their disease-causing or disease-potentiating functions. However, recently, attempts have been made to moderate the actual production of such proteins by interactions with molecules that direct their synthesis, such as intracellular RNA. By interfering with the production of proteins, maximum therapeutic effect and minimal side effects may be realized. It is the object of such therapeutic approaches to interfere with otherwise modulate gene expression leading to undesired protein formation.

One method for inhibiting specific gene expression is the use of oligonucleotides. Oligonucleotides are now accepted as therapeutic agents with great promise. Oligonucleotides are known to hybridize to single-stranded DNA or RNA molecules. Hybridization is the sequence-specific base pair hydrogen bonding of nucleobases of the oligonucleotide to the nucleobases of the target DNA or RNA molecule. Such nucleobase pairs are said to be complementary to one another. The concept of inhibiting gene expression through the use of sequence-specific binding of oligonucleotides to target RNA sequences, also known as antisense inhibition, has been demonstrated in a variety of systems, including living cells (f or example see: Wagner et al., *Science* (1993) 260: 1510–1513; Milligan et al., *J. Med. Chem.*, (1993) 36:1923–37; Uhlmann et al., *Chem. Reviews*, (1990) 90:543–584; Stein et al., *Cancer Res.*, (1988) 48:2659–2668).

The events that provide the disruption of the nucleic acid function by antisense oligonucleotides (Cohen in *Oligonucleotides: Antisense Inhibitors of Gene Expression*, (1989) CRC Press, Inc., Boca Raton, Fla.) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides: Miller and Ts'O, *Anti-Cancer Drug Design*, 1987, 2:117–128, and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Oligonucleotides may also bind to duplex nucleic acids to form triplex complexes in a sequence specific manner via Hoogsteen base pairing (Beal et al., *Science*, (1991) 251:1360–1363; Young et al., *Proc. Natl. Acad. Sci.* (1991) 88:10023–10026). Both antisense and triple helix therapeutic strategies are directed towards nucleic acid sequences that are involved in or responsible for establishing or maintaining disease conditions. Such target nucleic acid sequences may be found in the genomes of pathogenic organisms including bacteria, yeasts, fungi, protozoa, parasites, viruses, or may be endogenous in nature. By hybridizing to and modifying the expression of a gene important for the establishment, maintenance or elimination of a disease condition, the corresponding condition may be cured, prevented or ameliorated.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$) a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides may also be of therapeutic value when they bind to non-nucleic acid biomolecules such as intracellular or extracellular polypeptides, proteins, or enzymes. Such oligonucleotides are often referred to as "aptamers" and they typically bind to and interfere with the function of protein targets (Griffin et al., *Blood*, (1993), 81:3271–3276; Bock et al., *Nature*, (1992) 355: 564–566).

Oligonucleotides and their analogs have been developed and used for diagnostic purposes, therapeutic applications and as research reagents. For use as therapeutics, oligonucleotides must be transported across cell membranes or be taken up by cells, and appropriately hybridize to target DNA or RNA. These critical functions depend on the initial stability of the oligonucleotides toward nuclease degradation. A serious deficiency of unmodified oligonucleotides which affects their hybridization potential with target DNA or RNA for therapeutic purposes is the enzymatic degradation of administered oligonucleotides by a variety of intracellular and extracellular ubiquitous nucleolytic enzymes referred to as nucleases. For oligonucleotides to be useful as therapeutics or diagnostics, the oligonucleotides should demonstrate enhanced binding affinity to complementary target nucleic acids, and preferably be reasonably stable to nucleases and resist degradation. For a non-cellular use such as a research reagent, oligonucleotides need not necessarily possess nuclease stability.

A number of chemical modifications have been introduced into oligonucleotides to increase their binding affinity to target DNA or RNA and resist nuclease degradation.

Modifications have been made to the ribose phosphate backbone to increase the resistance to nucleases. These modifications include use of linkages such as methyl phosphonates, phosphorothioates and phosphorodithioates, and the use of modified sugar moieties such as 2'-O-alkyl ribose. Other oligonucleotide modifications include those made to modulate uptake and cellular distribution. A number of modifications that dramatic alter the nature of the internucleotide linkage have also been reported in the literature. These include non-phosphorus linkages, peptide nucleic acids (PNA's) and 2'–5' linkages. Another modification to oligonucleotides, usually for diagnostic and research applications, is labeling with non-isotopic labels, e.g., fluorescein, biotin, digoxigenin, alkaline phosphatase, or other reporter molecules.

A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability. In order to make effective therapeutics therefore this binding and hybrid stability of antisense oligonucleotides needs to be improved.

Of the large number of modifications made and studied, few have progressed far enough through discovery and development to deserve clinical evaluation. Reasons underlying this include difficulty of synthesis, poor binding to target nucleic acids, lack of specificity for the target nucleic acid, poor in vitro and in vivo stability to nucleases, and poor pharmacokinetics. Several phosphorothioate oligonucleotides and derivatives are presently being used as antisense agents in human clinical trials for the treatment of various disease states. A submission for approval was recently made to both United States and European regulatory agencies for one antisense drug, Fomivirsen, for use to treat cytomegalovirus (CMV) retinitis in humans.

The structure and stability of chemically modified nucleic acids is of great importance to the design of antisense oligonucleotides. Over the last ten years, a variety of synthetic modifications have been proposed to increase nuclease resistance, or to enhance the affinity of the antisense strand for its target mRNA (Crooke et al., *Med. Res. Rev.*, 1996, 16, 319–344; De Mesmaeker et al., *Acc. Chem. Res.*, 1995, 28, 366–374). Although a great deal of information has been collected about the types of modifications that improve duplex formation, little is known about the structural basis for the improved affinity observed.

RNA exists in what has been termed "A Form" geometry while DNA exists in "B Form" geometry. In general, RNA:RNA duplexes are more stable, or have higher melting temperatures ($T_m$) than DNA:DNA duplexes (Sanger et al., *Principles of Nucleic Acid Structure*, 1984, Springer-Verlag; New York, N.Y.; Lesnik et al., *Biochemistry*, 1995, 34, 10807–10815; Conte et al., *Nucleic Acids Res.*, 1997, 25, 2627–2634). The increased stability of RNA has been attributed to several structural features, most notably the improved base stacking interactions that result from an A-form geometry (Searle et al., *Nucleic Acids Res.*, 1993, 21, 2051–2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry*, 1996, 35, 8489–8494).

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051–2056). The structure of a hybrid duplex is intermediate between A- and B-form geometries, which may result in poor stacking interactions (Lane et al., *Eur. J. Biochem.*, 1993, 215, 297–306; Fedoroff et al., *J. Mol. Biol.*, 1993, 233, 509–523; Gonzalez et al., *Biochemistry*, 1995, 34, 4969–4982; Horton et al., *J. Mol. Biol.*, 1996, 264, 521–533). The stability of a DNA:RNA hybrid is central to antisense therapies as the mechanism requires the binding of a modified DNA strand to a mRNA strand. To effectively inhibit the mRNA, the antisense DNA should have a very high binding affinity with the mRNA. Otherwise the desired interaction between the DNA and target mRNA strand will occur infrequently, thereby decreasing the efficacy of the antisense oligonucleotide.

One synthetic 2'-modification that imparts increased nuclease resistance and a very high binding affinity to nucleotides is the 2'-methoxyethoxy (MOE, 2'-OCH$_2$CH$_2$OCH$_3$) side chain (Baker et al., *J. Biol. Chem.*, 1997, 272, 11944–12000; Freier et al., *Nucleic Acids Res.*, 1997, 25, 4429–4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429–4443). 2'-O-Methoxyethyl-substituted also have been shown to be antisense inhibitors of gene expression with promising features for in vivo use (Martin, *Helv. Chim. Acta*, 1995, 78, 486–504; Altmann et al., *Chimia*, 1996, 50, 168–176; Altmann et al., *Biochem. Soc. Trans.*, 1996, 24, 630–637; and Altmann et al., *Nucleosides Nucleotides*, 1997, 16, 917–926). Relative to DNA, they display improved RNA affinity and higher nuclease resistance. Chimeric oligonucleotides with 2'-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE-substituted oligonucleotide is currently available for the treatment of CMV retinitis.

Although the known modifications to oligonucleotides, including the use of the 2'-O-methoxyethyl modification, have contributed to the development of oligonuclotides for use in diagnostics, therapeutics and as research reagents, there still exists a need in the art for further modifications to oligonucleotides having enhanced hybrid binding affinity and/or increased nuclease resistance.

SUMMARY OF THE INVENTION

In accordance with the present invention, oligomers containing guanidinium groups are provided. The present invention provides monomers of the formula:

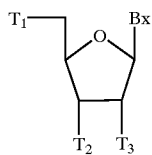

wherein:
Bx is a heterocyclic base;
$T_1$ is OH or a protected hydroxyl group;
$T_2$ is an activated phosphorus group or a linking moiety attached to a solid support;
$T_3$ is H, OH, a protected hydroxyl or a sugar substituent group;
said monomer further comprising at least one group, $R_1$, therein; said $R_1$ group occurring in lieu of at least one $T_1$, $T_2$ or $T_3$ or as a substituent on at least one Bx; said $R_1$ group having the formula:

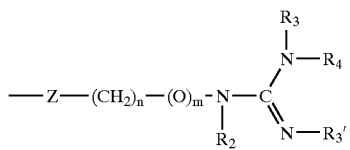

wherein:
each Z is, independently, a single bond, O, N or S;
each $R_2$, $R_3$, $R_{3'}$, and $R_4$ is, independently, hydrogen, $C(O)R_5$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or $R_3$ and $R_4$, together, are $R_7$;
each $R_5$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;
each $R_7$ is, independently, hydrogen or forms a phthalimide moiety with the nitrogen atom to which it is attached;
each m is, independently, zero or 1; and
each n is, independently, an integer from 1 to about 6.

Preferred compositions include oligomers comprising a plurality of nucleotide units of the structure:

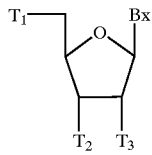

wherein:
Bx is a heterocyclic base;
each $T_1$, and $T_2$ is, independently, OH, a protected hydroxyl, a nucleotide, a nucleoside or an oligonucleotide;

$T_3$ is H, OH, a protected hydroxyl or a sugar substituent group;
said oligomer further comprising at least one group, $R_1$, therein; said $R_1$ group occurring at the 3' end, the 5' end, in lieu of at least one $T_3$ or as a substituent on at least one Bx; said $R_1$ group having the formula:

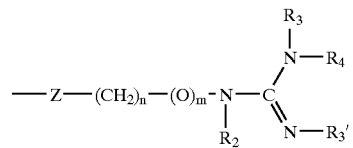

wherein:
each Z is, independently, a single bond, O, N or S;
each $R_2$, $R_3$, $R_{3'}$, and $R_4$ is, independently, hydrogen, $C(O)R_5$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or $R_3$ and $R_4$, together, are $R_7$;
each $R_5$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;
each $R_7$ is, independently, hydrogen or forms a phthalimide moiety with the nitrogen atom to which it is attached;
each m is, independently, zero or 1; and
each n is, independently, an integer from 1 to about 6.

In a preferred embodiment, $R_1$, $R_2$, $R_3$, $R_{3'}$, and $R_4$ are hydrogen. In another preferred embodiment, $R_1$, $R_2$, $R_3$, $R_{3'}$, and $R_4$ are hydrogen, m is zero and n is 2.

The present invention also provides methods for preparing oligomers comprising the steps of:

(a) selecting a monomer of the formula:

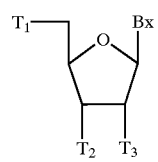

wherein:
Bx is a heterocyclic base;
$T_1$ is OH or a protected hydroxyl group;
$T_2$ is a linking moiety attached to a solid support;
$T_3$ is H, OH, a protected hydroxyl or a sugar substituent group;
said monomer further comprising at least one group, $R_1$, therein; said $R_1$ group occurring in lieu of at least one $T_1$, $T_2$ or $T_3$ or as a substituent on at least one Bx; provided that if $T_2$ is $R_1$, $T_3$ is a linking moiety attached to a solid support;

said R₁ group having the formula:

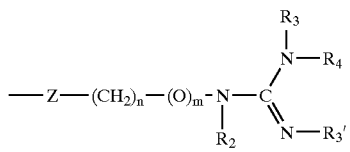

wherein:
    each Z is, independently, a single bond, O, N or S;
    each R₂, R₃, R₃', and R₄ is, independently, hydrogen, C(O)R₅, substituted or unsubstituted C₁–C₁₀ alkyl, substituted or unsubstituted C₂–C₁₀ alkenyl, substituted or unsubstituted C₂–C₁₀ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
    or R₃ and R₄, together, are R₇;
    each R₅ is, independently, substituted or unsubstituted C₁–C₁₀ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;
    each R₇ is, independently, hydrogen or forms a phthalimide moiety with the nitrogen atom to which it is attached;
    each m is, independently, zero or 1; and
    each n is, independently, an integer from 1 to about 6;
(b) deprotecting the protected hydroxyl group at the 5'-position to form a deprotected monomer;
(c) coupling said deprotected monomer with a second monomer of formula:

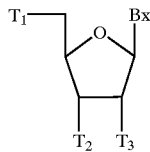

wherein:
    Bx is a heterocyclic base;
    T₁ is OH or a protected hydroxyl group;
    T₂ is an activated phosphorus group;
    T₃ is H, OH, a protected hydroxyl or a sugar substituent group;
said monomer further comprising at least one group, R₁, therein; said R₁ group occurring in lieu of at least one T₁, T₂ or T₃ or as a substituent on at least one Bx;
provided that if T₂ is R₁, T₃ is an activated phosphorus group; said R₁ group having the formula:

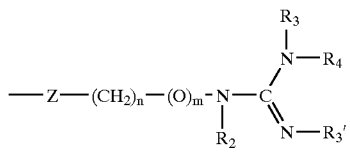

wherein:
    each Z is, independently, a single bond, O, N or S;
    each R₂, R₃, R₃', and R₄ is, independently, hydrogen, C(O)R₅, substituted or unsubstituted C₁–C₁₀ alkyl, substituted or unsubstituted C₂–C₁₀ alkenyl, substituted or unsubstituted C₂–C₁₀ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
    or R₃ and R₄, together, are R₇;
    each R₅ is, independently, substituted or unsubstituted C₁–C₁₀ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;
    each R₇ is, independently, hydrogen or forms a phthalimide moiety with the nitrogen atom to which it is attached;
    each m is, independently, zero or 1; and
    each n is, independently, an integer from 1 to about 6, said coupling occurring in the presence of an activating agent to form a coupled compound;
(d) capping said coupled compound with a capping reagent to form a capped compound having an internucleotide linkage;
(e) oxidizing said internucleotide linkage with an oxidizing reagent; and
(f) repeating steps (b) to (e) to form an oligomer. In one embodiment of the present invention, the method includes an additional step of cleaving the oligomer with a cleaving reagent.

Preferred activating reagents include tetrazole, pyridinium trifluoroacetate and dicyanoimidazole. It is preferred that acetic anhydride and N-methylimidazole be the capping reagent. Preferred oxidizing reagents include iodine, camphorsulfonyloxaziridine, t-butyl hydrogen peroxide and Beaucage reagent.

The present invention also provides compounds of the formula:

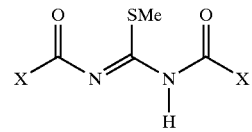

wherein X is cyanoethyloxy, benzyloxy, t-butoxy, methoxy, ethoxy, allyloxy, 9-fluorenylmethoxy, 2-(trimethylsilyl)-ethoxy, 2,2,2-trichloroethoxy, trifluoromethyl, butyryl, iso-butyryl, phenyl or aryl.

In one embodiment of the present invention, X is cyanoethyloxy. In another embodiment, X is phenyl. In yet another embodiment, X is t-butyl.

The present invention is also directed to non-nucleic acid monomers and oligomers comprising at least one such non-nucleic acid monomer. The present invention includes non-nucleic acid monomers of the formula:

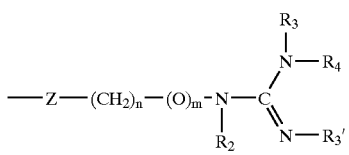

wherein:
X is $C_3$–$C_{10}$ alkyl, $C_6$–$C_{24}$ aryl, $C_6$–$C_{24}$ heteroaryl, $C_4$–$C_{20}$ alicyclic, $C_4$–$C_{20}$ alicyclic having at least one heteroatom, nucleoside, nucleotide or oligonucleotide;

$Y_1$ is a hydroxyl protecting group;

$Y_2$ is an activated phosphorus group or a linking moiety attached to a solid support;

each $R_2$, $R_3$, $R_{3'}$, and $R_4$ is, independently, hydrogen, $C(O)R_5$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or $R_3$ and $R_4$, together, are $R_7$;

each $R_5$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

each $R_7$ is, independently, hydrogen or forms a phthalimide moiety with the nitrogen atom to which it is attached; and n is an integer from 1 to about 6.

In a preferred embodiment, $Y_1$ is dimethoxytrityl. In another preferred embodiment, $Y_1$ is monomethoxytrityl. In yet another preferred embodiment, $Y_2$ is a phosphoramidite. In a further embodiment, $Y_2$ is a linking moiety attached to a solid support. It is preferred that $Y_2$ be succinyl CPG.

DETAILED DESCRIPTION OF PREFERRED EMBODIMENTS

Figure 1:
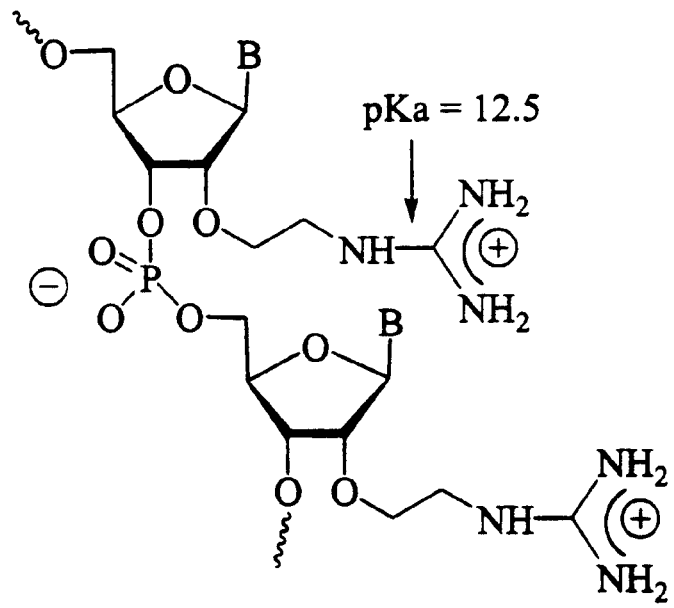
FIG. 1 shows the structure of a 2'-O-[2-(guanidinium)ethyl] modification.

The present invention provides monomers comprising a guanidinium functionality located at the 2'-position or as a substituent on the heterocyclic base. The present invention also provides oligomers containing a plurality of nucleotide units, at least one of said nucleotide units bearing a guanidinium group at the 3' end, the 5' end, the 2'-position, or as a substituent on the heterocyclic base. Also provided are methods of making such oligomers.

As used herein, "guanidinium group" or "guanidinium functionality" denotes a group of formula:

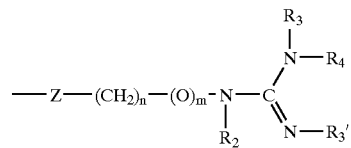

wherein:
Z is a single bond, O, N or S;

each $R_2$, $R_3$, $R_{3'}$, and $R_4$ is, independently, hydrogen, $C(O)R_5$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or $R_3$ and $R_4$, together, are $R_7$;

each $R_5$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

each $R_7$ is, independently, hydrogen or forms a phthalimide moiety with the nitrogen atom to which it is attached;

m is zero or 1; and n is an integer from 1 to about 6.

In one embodiment of the present invention, Z is O, $R_2$, $R_3$, $R_{3'}$, and $R_4$ are hydrogen, n is 1 and m is zero. This 2-O-guanidiniumethyl modification, present in an oligomer, significantly increases the binding affinity of the oligomer to the target. This increase in binding affinity improves when additional guanidinium modifications are dispersed within the oligomer. Guanidinium functionalized oligomers are of use in forming triple helices with double-stranded nucleic acids moieties.

The guanidinium group is strongly basic with a $pk_a$ of about 12.5, and is a well-stabilized cation with the positive charge being delocalized over four atoms. Guanidinium groups are understood to facilitate contact between proteins and peptides with phosphate groups of nucleic acids. Particularly, the guanidinium group is suggested to form ionic interactions with guanine residues in the major groove or bond with phosphate moieties located in the minor groove.

The present invention includes oligomers containing nucleotide monomers as well as non-nucleic acid monomers. For example, the present invention includes compounds of the following formulas, as well as oligomers having at least one monomer compound of the following formulas:

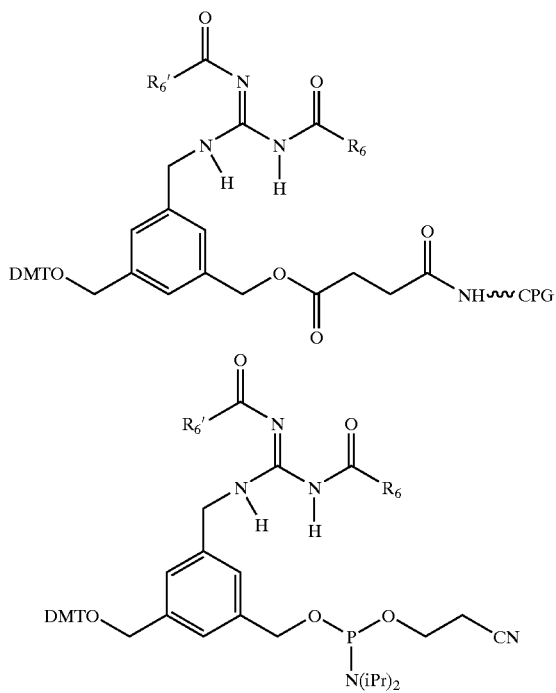

wherein each $R_6$ and $R_{6'}$ is, independently, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl.

Heterocyclic bases amenable to the present invention include both naturally- and non-naturally-occurring nucleobases and heterocycles. The heterocyclic base may be a pyrimidine, purine or diaminopurine base. A representative list includes adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 7-methylguanine, 5-trifluoromethyl and other 5-substituted uracils and cytosines. Further heterocyclic bases include those disclosed in U.S. Pat. No. 3,687,808; the *Concise Encyclopedia Of Polymer Science And Engineering*, pages 858–859, Kroschwitz, J. I., Ed., John Wiley & Sons, 1990; and Englisch et al., *Angewandte Chemie, International Edition*, 1991, 30, 613.

Heterocyclic bases in the oligomers of the present invention may be covalently bound to an $R_1$ group. In a preferred embodiment, the $R_1$ group may be covalently attached to C5 or an amino group at the 4-position of a pyrimidine heterocyclic base. In another preferred embodiment, the $R_1$ group may be covalently attached to an amino group at the 2-position or 6-position of a purine heterocyclic base. The $R_1$ group may even be attached to the amino group at the 6-position of a diaminopurine heterocyclic base.

The monomers of the present invention can include appropriate activated phosphorus groups such as activated phosphate groups and activated phosphite groups. As used herein, the terms activated phosphate and activated phosphite groups refer to activated monomers or oligomers that are reactive with a hydroxyl group of another monomeric or oligomeric compound to form a phosphorus-containing internucleotide linkage. Such activated phosphorus groups contain activated phosphorus atoms in $P^{III}$ or $P^V$ valency states. Such activated phosphorus atoms are known in the art and include, but are not limited to, phosphoramidite, H-phosphonate and phosphate triesters. A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods to yield, in a preferred embodiment, phosphodiester or phosphorothioate internucleotide linkages. Additional activated phosphates and phosphites are disclosed in Tetrahedron Report Number 309 (Beaucage and Iyer, *Tetrahedron*, 1992, 48, 2223–2311).

In the context of the present invention, the term "oligonucleotide" refers to an oligomer or polymer of ribonucleic acid (RNA) or deoxyribonucleic acid (DNA) or mimics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Although antisense oligonucleotides are a preferred form of antisense compounds, the present invention comprehends other oligomeric antisense compounds, including but not limited to oligonucleotide mimics. The oligomers in accordance with this invention preferably comprise from about 8 to about 30 nucleobases (i.e., from about 8 to about 30 linked nucleosides). Particularly preferred oligomers are antisense oligonucleotides, even more preferably those comprising from about 12 to about 25 nucleobases. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure. Open linear structures are generally preferred. Within the oligonucleotide structure, the phosphate groups are commonly referred to as forming the internucleotide backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleotide linkages. As defined in this specification, oligonucleotides having modified backbones include those that retain a phosphorus atom in the backbone and those that do not have a phosphorus atom in the backbone. In the context of the present invention, and as sometimes referenced in the art, modified oligonucleotides that do not have a phosphorus atom in the internucleotide backbone can also be considered to be oligonucleosides.

Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylenephosphonates and chiral phosphonates, phosphinates, phosphoramidates including 3'-aminophosphoramidates and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3', or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These linkages include morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application.

In other preferred oligonucleotide mimics, both the sugar and the internucleoside linkage, i.e., the backbone of the nucleotide units, are replaced with novel groups. The base units are maintained for hybridization with an appropriate nucleic acid target compound. One such oligomeric compound, an oligonucleotide mimic that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teachings of PNA compounds can be found in Nielsen et al. (*Science,* 1991, 254, 1497–1500).

In one embodiment of the present invention, oligonucleotides with phosphorothioate backbones are preferred. Also preferred are oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The methods according to the present invention are performed in various traditional solvents either utilizing solution phase techniques or automated synthetic protocols. Many solvents for automated oligonucleotide synthesis as well as solution phase oligonucleotide synthesis are known in the art. Preferred solvents include DMF, DMSO, THF, THP and $CH_3CN$.

Standard solution phase and solid phase methods for the synthesis of oligonucleotides and oligonucleotide analogs are well known to those skilled in the art. These methods are constantly being improved in ways that reduce the time and cost required to synthesize these complicated compounds. Representative solution phase techniques are described in U.S. Pat. No. 5,210,264, issued May 11, 1993 and commonly assigned with this invention. Representative solid phase techniques employed for oligonucleotide and oligonucleotide analog synthesis utilizing standard phosphoramidite chemistries are described in "Protocols For Oligonucleotides And Analogs," Agrawal, S., Ed., Humana Press, Totowa, N.J., 1993.

A preferred method of choice for the preparation of naturally-occurring oligonucleotides, as well as non-naturally-occurring (or modified) oligonucleotides such as phosphorothioate oligonucleotides, is via solid-phase synthesis wherein an oligonucleotide is prepared on a polymer support (a solid support) such as controlled pore glass (CPG); oxalyl-controlled pore glass (see, e.g., Alul et al., *Nucleic Acids Research* 1991, 19, 1527); TENTAGEL Support, (see, e.g., Wright et al., *Tetrahedron Letters* 1993, 34, 3373); or POROS, a polystyrene resin available from PerSeptive Biosystems. Equipment for such synthesis is commercially available from several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), *Oligonucleotides and Analogues, a Practical Approach*, Oxford University Press, New York (1991).

Solid-phase synthesis relies on sequential addition of nucleotides to one end of a growing oligonucleotide chain. Typically, a first nucleoside (having protecting groups on any exocyclic amine functionalities present) is attached to an appropriate glass bead support. Activated phosphite compounds (typically nucleotide phosphoramidites, also bearing appropriate protecting groups) are added stepwise to elongate the growing oligonucleotide. Additional methods for solid-phase synthesis may be found in U.S. Pat. Nos. 4,415,732; 4,458,066; 4,500,707; 4,668,777; 4,973,679; 5,132,418; 4,725,677 and Re. 34,069.

A representative list of chemical functional groups according to the invention include $C_1$–$C_{10}$ alkyl, substituted $C_1$–$C_{10}$ alkyl, $C_2$–$C_{25}$ alkenyl, substituted $C_2$–$C_{25}$ alkenyl, $C_2$–$C_{15}$ alkynyl, substituted $C_2$–$C_{15}$ alkynyl, $C_4$–$C_7$ carbocyclic alkyl, substituted carbocyclic alkyl, alkenyl carbocyclic, substituted alkenyl carbocyclic, alkynyl carbocyclic, substituted alkynyl carbocyclic, $C_6$–$C_{20}$ aryl, substituted $C_6$–$C_{20}$ aryl, heteroaryl, substituted heteroaryl, a nitrogen, oxygen, or sulfur containing heterocycle, a substituted nitrogen, oxygen, or sulfur containing heterocycle, a mixed heterocycle, or a substituted mixed heterocycle, where said substituent groups are selected from alkyl, alkenyl, alkynyl, aryl, hydroxyl, amino, alkoxy, carboxy, benzyl, nitro, thiol, thioalkyl, thioalkoxy, or halogen groups; or L is phthalimido, an ether having 2 to 10 carbon atoms and 1 to 4 oxygen or sulfur atoms, a metal coordination group, a conjugate group, halogen, hydroxyl, thiol, keto, carboxyl, $NR^1R^2$, $CONR^1$, amidine ($C(=NH)NR^2R^3$), guanidine ($NHC(=NH)NR^2R^3$), glutamyl ($R_1OOCCH$ ($NR^2R^3$) ($CH_2)_2C(=O)$, nitrate, nitro, nitrile, trifluoromethyl, trifluoromethoxy, NH-alkyl, N-dialkyl, O-aralkyl, S-aralkyl, NH-aralkyl, azido ($N_3$), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a drug, or a group capable of hydrogen bonding, wherein each $R^1$ and $R^2$ is, independently, H, haloalkyl, $C_1$–$C_{10}$ alkyl, $C_2$–$C_{10}$ alkenyl, $C_2$–$C_{10}$ alkynyl, or $C_6$–$C_{14}$ aryl; and each $R^3$ is, independently, a single bond, CH=CH, C≡C, O, S, $NR^6$, $SO_2$, $C_6$–$C_{14}$ aryl, substituted $C_6$–$C_{14}$ aryl, heteroaryl, substituted heteroaryl, a nitrogen, oxygen, or sulfur containing heterocycle, a substituted nitrogen, oxygen, or sulfur containing heterocycle, a mixed heterocycle, or a substituted mixed heterocycle, wherein said substituent groups are selected from hydroxyl (OH), amino, alkoxy, carboxy, benzyl, phenyl, nitro ($NO_2$), thiol (SH), thioalkoxy, halogen, alkyl, aryl, alkenyl, and alkynyl groups.

A number of chemical functional groups can be introduced into compounds of the present invention in a blocked form and can then be subsequently deblocked to form the final, desired compound. In general, a blocking group renders a chemical functionality of a molecule inert to specific reaction conditions and can later be removed from such functionality in a molecule without substantially damaging the remainder of the molecule (Green and Wuts, Protective Groups in Organic Synthesis, 2d edition, John Wiley & Sons, New York, 1991). For example, amino groups can be blocked as phthalimido, 9-fluorenylmethoxycarbonyl (FMOC), triphenylmethylsulfenyl, t-BOC or benzyl groups. Carboxyl groups can be protected as acetyl groups.

Representative hydroxyl protecting groups are described by Beaucage et al. (*Tetrahedron* 1992, 48, 2223). Preferred hydroxyl protecting groups are acid-labile, such as trityl, monomethoxytrityl, dimethoxytrityl, trimethoxytrityl, 9-phenylxanthine-9-yl (Pixyl) and 9-(p-methoxyphenyl)-xanthine-9-yl (MOX). Chemical functional groups can also be "blocked" by including them in a precursor form. Thus an azido group can be considered to be a "blocked" form of an amine as the azido group may be easily converted to the amine. Further representative protecting groups utilized in oligonucleotide synthesis are discussed in Agrawal et al., Protocols for Oligonucleotide Conjugates, Humana Press, New Jersey, 1994, Vol. 26, pp. 1–72.

In the context of the present invention, a "heterocycle" is a cyclic compound containing at least one heteroatom such as N, O or S. A "mixed heterocycle" is a cyclic compound containing at least two heteroatoms such as N, O or S. A "heteroaryl" compound is a heterocycle containing at least one heteroatom such as N, O or S and is not fully saturated, e.g., is in a state of partial or complete saturation. "Heteroaryl" is also meant to include fused systems including systems where one or more of the fused rings contain no heteroatoms. Heterocycles, including nitrogen heterocycles, according to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, indole, and carbazole groups.

As used herein, "linking moiety" refers to a hydrocarbyl chain which connects the monomers and oligomers of the invention to a solid support. A preferred linking moiety is a succinyl group. Other linking moieties include, but are not limited to, substituted or unsubstituted $C_1$–$C_{10}$ alkyl, substituted or unsubstituted $C_2$–$C_{10}$ alkenyl or substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl.

"Conjugate groups" according to the present invention include those known in the art. A representative list of conjugate groups amenable to the present invention includes intercalators, reporter molecules, contrast reagents, cleaving agents, cell targeting agents, cyanine dyes, polyamines, polyamides, poly ethers including polyethylene glycols, and other moieties known in the art for enhancing the pharmacodynamic properties or the pharmacokinetic properties. Typical conjugate groups include PEG groups, cholesterols, phospho-lipids, biotin, phenanthroline, phenazine, pyrene, retinal, phenanthridine, anthraquinone, acridine, fluoresceins, rhodamines, coumarins, and dyes.

For the purposes of this invention, the term "reporter molecule" includes molecules or enzymes that have physical or chemical properties that allow them to be identified in gels, fluids, whole cellular systems, broken cellular systems and the like utilizing physical properties such as spectroscopy, radioactivity, colorimetric assays, fluorescence, and specific binding. Particularly useful as reporter molecules are fluorophores, chromophores and radiolabel-containing moieties.

Fluorophores are molecules detectable by fluorescence spectroscopy. Examples of preferred fluorophores are fluorescein and rhodamine dyes and acridines. There are numerous commercial available fluorophores including "Texas Red" and other like fluoresceins and rhodamines available from Molecular Probes, Eugene, Oreg.

Chromophores are molecules capable of detection by visible or ultraviolet (UV-VIS) absorbance spectroscopy. Examples of chromophores are polynuclear aromatics such as anthracene, perylene, pyrene, rhodamine and chrysene.

Radiolabel-containing moieties, as used herein, are molecules incorporating at least one radioactive atom, such as $^3H$ or $^{14}C$, enabling detection thereby.

Reporter enzymes may be detected directly or via their enzymatic products by any of the methods mentioned above.

Particularly useful as reporter enzymes are alkaline phosphatase and horseradish peroxidase.

Intercalators are polycyclic aromatic moieties that can insert between adjacent base pairs without affecting normal Watson-Crick base pairing, and include hybrid intercalator/ligands such as the photonuclease/intercalator ligand 6-[[[9-[[6-(4-nitrobenzamido)hexyl]amino]acridin-4-yl]carbonyl]amino]hexanoylpentafluorophenyl ester. This compound has two noteworthy features: an acridine moiety that is an intercalator and a p-nitrobenzamido group that is a photonuclease. Other representative intercalators are disclosed by Manoharan, M., *Antisense Research and Applications*, Crooke and Lebleu, eds., CRC Press, Boca Raton, 1993.

In the context of this invention, "hybridization" means hydrogen bonding, which may be Watson-Crick, Hoogsteen or reversed Hoogsteen hydrogen bonding, between complementary heterocyclic bases. "Complementary," as used herein, refers to the capacity for precise pairing between two heterocyclic bases. For example, adenine and thymine are complementary bases which pair through the formation of hydrogen bonds. "Complementary" and "specifically hybridizable," as used herein, refer to precise pairing or sequence complementarity between a first and a second nucleic acid-like oligomer containing nucleoside subunits. For example, if a heterocyclic base at a certain position of the first nucleic acid is capable of hydrogen bonding with a heterocyclic base at the same position of the second nucleic acid, then the first nucleic acid and the second nucleic acid are considered to be complementary to each other at that position. The first and second nucleic acids are complementary to each other when a sufficient number of corresponding positions in each molecule are occupied by bases which can hydrogen bond with each other. Thus, "specifically hybridizable" and "complementary" are terms which are used to indicate a sufficient degree of complementarity such that stable and specific binding occurs between a compound of the invention and a target nucleic acid molecule. It is understood that an oligomer of the invention need not be 100% complementary to its target nucleic acid to be specifically hybridizable. An oligomer is specifically hybridizable when binding of the oligomer to the target nucleic acid interferes with the normal function of the target to cause a loss of utility, and there is a sufficient degree of complementarity to avoid non-specific binding of the oligomer to non-target sequences under conditions in which specific binding is desired, i.e. under physiological conditions in the case of in vivo assays or therapeutic treatment, or in the case of in vitro assays, under conditions in which the assays are performed.

In the context of the present invention, "modulating" means altering or modifying, and includes increasing or decreasing. Accordingly, modulating gene expression means increasing or decreasing gene expression. In one aspect of the invention, modulating gene expression means decreasing gene expression.

As used herein the term "sugar substituent group" or "2'-substituent group" includes groups attached to the 2' position of the ribosyl moiety with or without an oxygen atom. 2'-Sugar modifications amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and PEG-containing groups, such as crown ethers, and other reported substituent groups. See, Ouchi et al., *Drug Design and Discovery* 1992, 9, 93; Ravasio et al., *J. Org. Chem.* 1991, 56, 4329; and Delgardo et al., *Critical Reviews in Therapeutic Drug Carrier Systems* 1992, 9, 249. Further sugar substituent groups are disclosed by Cook (*Anti-Cancer Drug Design*, 1991, 6, 585–607). Fluoro, O-alkyl, O-alkylamino, O-alkyl imidazole, O-alkylaminoalkyl, and alkyl amino substituents are described in U.S. Pat. No. 6,166,197, filed Mar. 6, 1995, entitled "Oligomeric Compounds having Pyrimidine Nucleotide(s) with 2' and 5' Substitutions."

Additional 2' sugar modifications amenable to the present invention include 2'-SR and 2'-NR$_2$ groups, where each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997. The incorporation of 2'-SR monomer synthons are disclosed by Hamm et al., *J. Org. Chem.*, 1997, 62, 3415–3420. 2'-NR$_2$ nucleosides are disclosed by Goettinigen, M., *J. Org. Chem.*, 1996, 61, 6273–6281; and Polushin et al., *Tetrahedron Lett.*, 1996, 37, 3227–3230. Further representative 2'-O-sugar modifications amenable to the present invention include those having one of formula I or II:

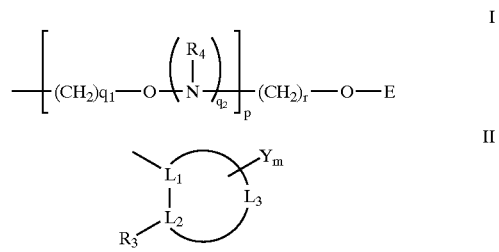

wherein:

E is C$_1$–C$_{10}$ alkyl, N(R$_8$)(R$_9$) or N=C(R$_8$)(R$_9$);

each R$_8$ and R$_9$ is, independently, H, C$_1$–C$_{10}$ alkyl, a nitrogen protecting group, or R$_8$ and R$_9$, together, are a nitrogen protecting group or are joined in a ring structure that includes at least one additional heteroatom selected from N and O;

R$_{10}$ is OX, SX, or N(X)$_2$;

each X is, independently, H, C$_1$–C$_8$ alkyl, C$_1$–C$_8$ haloalkyl, C(=NH)N(H)Z, C(=O)N(H)Z or OC(=O)N(H)Z;

Z is H or C$_1$–C$_8$ alkyl;

L$_1$, L$_2$ and L$_3$ comprise a ring system having from about 4 to about 7 carbon atoms or having from about 3 to about 6 carbon atoms and 1 or 2 heteroatoms, said heteroatoms being selected from oxygen, nitrogen and sulfur, wherein said ring system is aliphatic, unsaturated aliphatic, aromatic, or saturated or unsaturated heterocyclic;

Y is C$_1$–C$_{10}$ alkyl or haloalkyl, C$_2$–C$_{10}$ alkenyl, C$_2$–C$_{10}$ alkynyl, C$_6$–C$_{14}$ aryl, N(R$_8$) (R$_9$) OR$_8$, halo, SR$_8$ or CN;

each q$_1$ is, independently, an integer from 2 to 10;

each q$_2$ is 0 or 1;

p is an integer from 1 to 10; and r is an integer from 1 to 10;

provided that when p is 0, r is greater than 1.

Representative 2'-O-sugar substituents of formula I are disclosed in U.S. Pat. No. 6,172,209, filed Aug. 7, 1998, entitled "Capped 2'-Oxyethoxy Oligonucleotides," hereby incorporated by reference in its entirety.

Representative cyclic 2'-O— sugar substituents of formula II are disclosed in U.S. Pat. No. 6,271,356, filed Jul.

27, 1998, entitled "RNA Targeted 2'-Modified Oligonucleotides that are Conformationally Preorganized."

In the context of the present invention, "alkyl" means substituted or unsubstituted hydrocarbyl groups wherein the carbon atoms are connected via single bonds. "Alkenyl" means substituted or unsubstituted hydrocarbyl moieties having at least one double bond. "Alkynyl" means substituted or unsubstituted hydrocarbyl moieties having at least one triple bond.

Another modification that is used to prepare oligomeric compounds amenable to the present invention includes locked nucleic acids (LNA's) which are novel conformationally restricted oligonucleotide analogs containing 2'-O, 4'-C-methylene LNA monomers (see, Singh et al., *Chem. Commun.*, 1998, 4, 455–456). LNA and LNA analogs display very high duplex thermal stabilities with complementary DNA and RNA (Tm=+3 to +10 C), stability towards 3'-exonucleolytic degradation, and good solubility properties.

Synthesis of the LNA monomers adenine, cytosine, guanine, 5-methylcytosine, thymine and uracil, their oligomerization, and nucleic acid recognition properties have been described (see Koshkin et al., *Tetrahedron*, 1998, 54, 3607–3630). Studies of mis-matched sequences show that LNA obey the Watson-Crick base pairing rules with generally improved selectivity compared to the corresponding unmodified reference strands.

Potent and nontoxic antisense oligonucleotides containing LNA's have been described (Wahlestedt et al., *Proc. Natl. Acad. Sci. U.S.A.*, 2000, 97, 5633–5638.) The authors have demonstrated that LNA's confer several desired properties to antisense agents. LNA/DNA copolymers were not degraded readily in blood serum and cell extracts. LNA/DNA copolymers exhibited potent antisense activity on assay systems as disparate as a G-protein-coupled receptor in living rat brain and an *Escherichia coli* reporter gene.

The conformations of LNA's has been determined by 2D NMR spectroscopy to show that the locked conformation of the LNA nucleotides both in ssLNA and in the duplexes organize the phosphate backbone in such a way as to introduce higher population of the N-type conformation (See, Petersen et al., *J. Mol. Recognit.*, 2000, 13, 44–53). These conformational changes are associated with improved stacking of the nucleobases (see also, Wengel et al., *Nucleosides Nucleotides*, 1999, 18, 1365–1370).

LNA's form duplexes with complementary DNA, RNA or LNA with high thermal affinities. CD spectra show that duplexes involving fully modified LNA (esp. LNA:RNA) structurally resemble an A-form RNA:RNA duplex. NMR examination of an LNA:DNA duplex confirm the 3'-endo conformation of an LNA monomer. Recognition of double-stranded DNA is demonstrated suggesting strand invasion by LNA. Lipofectin-mediated efficient delivery of LNA into living human breast cancer cells has been accomplished.

Preparation of locked nucleoside analogs-containing oligodeoxyribonucleotide duplexes as substrates for nucleic acid polymerases has been described (see, Wengel et al., PCT International Application WO 98-DK393 19980914). The novel type of LNA modified oligonucleotides, as well as the LNAs as such, are useful in a wide range of diagnostic applications as well as therapeutic applications. Among these are included antisense applications, PCR applications, strand displacement oligomers, as substrates for nucleic acid polymerases, and as nucleotide based drugs.

LNA has been shown to form exceedingly stable LNA:LNA Duplexes (Koshkin et al., *J. Am. Chem. Soc.*, 1998, 120, 13252–13253). LNA:LNA hybridization was shown to be the most thermally stable nucleic acid type duplex system, and the RNA-mimicking character of LNA was established at the duplex level. Introduction of 3 LNA monomers (T or A) induced significantly increase melting points (T=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

Synthesis of 2'-amino-LNA, a novel conformationally restricted high-affinity oligonucleotide analog with a Handle has been shown (see Singh et al., *J. Org. Chem.*, 1998, 63, 10035–10039.)

2'-Amino- and 2'-methylamino-LNA's were prepared and thermal stability of their duplexes with complementary RNA and DNA strands have been previously reported. Similarly, The first analogs of LNA, phosphorothioate-LNA and 2'-thio-LNAs have been prepared (see Kumar et al., *Bioorg. Med. Chem. Lett.*, 1998, 8, 2219–2222.)

As used herein, "alicyclic" means hydrocarbyl groups having a saturated cyclic structure wherein the carbon atoms are connected by single bonds. Alicyclic groups according to the present invention may also contain heteroatoms within the cyclic structure or as part of an exocyclic substituent.

Further, in the context of the present invention, "aryl" (generally $C_6$–$C_{24}$) includes, but is not limited to, substituted and unsubstituted aromatic hydrocarbyl groups. Aralkyl groups (generally $C_7$–$C_{25}$) include, but are not limited to, groups having both aryl and alkyl functionalities, such as benzyl and xylyl groups. Preferred aryl and aralkyl groups include, but are not limited to, phenyl, benzyl, xylyl, naphthyl, toluoyl, pyrenyl, anthracyl, azulyl, phenethyl, cinnamyl, benzhydryl, and mesityl. Typical substituents for substitution include, but are not limited to, hydroxyl, amino, alkoxy, carboxy, benzyl, phenyl, nitro, thiol, thioalkoxy, halogen, alkyl, aryl, alkenyl, or alkynyl groups.

Formulation of therapeutic compositions utilizing compounds of the present invention and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 ug to about 10 g per kg of body weight, once or more daily, to once every 20 years.

Additional objects, advantages and novel features of the present invention will become apparent to those skilled in the art upon examination of the following examples. The following examples illustrate the invention and are not intended to limit the same. Those skilled in the art will recognize, or be able to ascertain through routine experimentation, numerous equivalents to the specific substances, compositions and procedures described herein. Such equivalents are considered to be within the scope of the present invention.

EXAMPLES

All reagents and solvents were purchased from commercial sources unless otherwise noted. 2-Cyanoethanol, N,N'-disuccinimidyl carbonate (DSC), N-(2-hydroxy)-phthalimide, 2-cyanoethyl-N,N,N',N'-tetraisopropylphosphoro-diamidite, 6-amino-hexanol and 2-methyl-2-thiopseudourea-sulfate were obtained from Aldrich Chemical Co., Inc. (Milwaukee, Wis.). Reagents for the DNA synthesizer were purchased from PerSeptive Biosystems, Inc. (Framingham, Mass.). 2,2'-Anhydro-5-methyluridine was purchased from Ajinomoto (Tokyo, Japan). Flash chromatography was performed on silica gel (Baker, 40 mm). Thin-layer chromatography was performed on Kieselgel glass plates from E. Merck and visualized with UV light and p-anisaldehyde/sulfuric acid/acetic acid spray followed by charring.

For all derivatizations described herein, the derivatized material can be used as obtained without further purification.

Example 1

Synthesis of N-(2-cyanoethoxycarbonyloxy) succinimide(CEOC-O-Succinimide) (1)

To a stirred solution of 2-cyanoethanol (7.23 g, 102 mmol) in 300 mL of anhydrous $CH_3CN$, under argon atmosphere, N,N'-disuccinimidyl carbonate (34.0 g, 133 mmol) was added followed by pyridine (11.3 mL, 140 mmol). The suspension became a clear solution after about 1 h. The solution was stirred for an additional 6 h and then concentrated in vacuo. The residue was redissolved in dichloromethane (200 mL), extracted with saturated $NaHCO_3$ solution (3×50 mL) followed by saturated NaCl solution (3×50 mL). The organic layer was dried (anhydrous $Na_2SO_4$) and concentrated to afford a white solid. Traces of pyridine were removed by co-evaporation with dry acetonitrile. The white solid was dried overnight in vacuo and then triturated with ether (150 mL) to yield 20.23 g (94%) of 1 as a colorless amorphous powder. This material is stable at room temperature in a desiccator for an extended period (1–2 years). The proton and carbon NMR spectra revealed a homogeneous material even at this stage. The material was further purified by chromatography on silica gel using $CH_2Cl_2$:EtOAc (50:50) to give a white crystalline compound (18.72 g, 87%); $R_f$=0.21; m.p. 105.5° C.

1H NMR (400 MHz, $CDCl_3$): 2.85 (t, J=6.62 Hz, 2H), 2.86 (s, 4H), 4.45 (t, J=5.96 Hz); $^{13}C$ NMR (80 MHz, DMSO-$d_6$): 17.33, 25.39, 65.86, 117.91, 150.91, 169.82; HRMS(FAB): Calcd for $C_8H_9N_2O_5^+$ 213.0511, Found: 213.0509; Anal: Calcd for $C_8H_8N_2O_5$: C, 45.29; H, 3.80; N, 13.20; Found: C, 45.19; H, 3.45; N, 13.02.

Example 2

Synthesis of 2'-O-phthalimidoethyl-5-methyluridine (2)

N-(2-Hydroxyethyl)phthalimide (277 g, 1.45 mol) was slowly added to a solution of borane in tetrahydrofuran (1 M, 600 mL), with stirring. Hydrogen gas evolved as the solid dissolved. Once the rate of gas evolution subsided, the solution was placed in a 2 L stainless steel bomb. 2,2'-Anhydro-5-methyluridine (60 g, 0.25 mol) and sodium bicarbonate (120 mg) were added and the bomb was sealed. After 30 minutes, the bomb was vented and placed in an oil bath and heated to 150° C. internal temperature for 24 h. The bomb was cooled to room temperature and opened. TLC (ethyl acetate-methanol; 95:5) revealed the disappearance of starting material. The crude solution was concentrated and the residue was purified by chromatography on silica gel starting with ethyl acetate to remove the excess phthalimide reagent, followed by ethyl acetate-methanol (95:5) to elute 2 (22.2 g, 20.6%).

1H NMR (200 MHz, DMSO-$d_6$): 1.8 (s, 3H), 3.4–4.2 (m, 6H), 5.0–5.2 (m, 2H), 5.8 (d, J=5.1 Hz, 1H), 7.65 (s, 1H), 7.8–8.0 (m, 4H), 11.2 (s, 1H).

Example 3

Synthesis of 2'-O-(2-phthalimidoethyl)-5'-O-(4,4'-dimethoxy-trityl)-5-methyl Uridine (3)

2'-O-Phthalimidoethyl-5-methyluridine (2, 22.2 g, 0.053 mol) was coevaporated with pyridine (2×75 mL) and then dissolved in 100 mL of pyridine. Dimethoxytrityl chloride (27 g, 0.080 mol) was added in one portion, with stirring, TLC (ethyl acetate-hexanes 50:50), after 1 h, indicated completion of the reaction. Methanol (10 mL) was added to quench the reaction. The mixture was concentrated and the residue was partitioned between ethyl acetate and saturated sodium bicarbonate solution (150 mL each). The organic layer was concentrated and the residue was dissolved in a minimum amount of dichloromethane and applied to a silica gel column. The compound was eluted with ethyl acetate-hexanes-triethylamine (50:50:1 to 80:20:1) to give 3 (26.1 g, 68%) as a white foam.

1H NMR (200 MHz, $CDCl_3$): 1.33 (s, 3H), 3.05 (d, J=8.4 Hz, 1H), 3.49 (m, 2H), 3.8 (s, 6H), 3.9–4.1 (m, 4H), 4.18–4.26 (m, 1H), 4.47 (m, 1H), 5.88 (s, 1H), 6.84 (d, J=8.78 Hz, 4H), 7.22–7.43 (m, 9H), 7.69–7.88 (m, 5H), 8.26 (s, 1H); HRMS(FAB): Calcd for $C_{41}H_{39}N_3O_{10}Na^+$ 756.2533, Found: 756.2553.

Example 4

Synthesis of 2'-O-(2-aminoethyl)-5'—O— (4,4'-dimethoxytrityl)-5-methyluridine (4)

2'-O-Phthalimidoethyl-5'-O-DMT-5-methyluridine (3, 21.1 g, 0.029 mol) was dissolved in methanol (500 mL). Anhydrous hydrazine (4.9 mL, 0.15 mol) was added and the solution was heated to reflux. TLC after 3 h indicated a complete reaction. The residue was purified by chromatography on silica gel using methanol and then methanol-ammonium hydroxide (98:2) to give 4 (12.4 g, 70%). The material was completely soluble in methylene chloride and traces of silica from leaching of the column were removed by filtration at this stage and reevaporating the solution.

1H NMR (200 MHz, $CDCl_3$): 1.39 (s, 3H), 2.98 (t, J=3.48 Hz, 2H), 3.45 (d, J=2.56 Hz, 1H), 3.53 (d, J=1.96 Hz, 1H), 3.56–3.68 (m, 2H), 3.81 (s, 6H), 3.99 (m, 1H), 4.1 (t, J=4.56 Hz, 1H), 4.17 (m, 1H), 4.45 (t, J=5.06 Hz, 1H), 6.06 (d, J=4.12 Hz, 1H), 6.86 (d, J=8.9 Hz, 4H), 7.25–7.46 (m, 9H), 7.67 (s, 1H); $^{13}C$ (50 MHz, $CDCl_3$): 11.71, 40.55, 45.76, 55.03, 62.47, 69.15, 70.65, 82.64, 83.49, 86.62, 87.10, 110.98, 113.09, 126.91, 127.77, 127.97, 129.95, 135.35, 144.25, 151.27, 158.46, 164.97; HRMS (FAB): Calcd for $C_{33}H_{37}O_8N_3Na$- 626.2478, Found: 626.2501.

Example 5

Synthesis of N,N'-bis-CEOC-2-methyl-2-thiopseudourea (5)

2-Methyl-2-thiopseudourea.½$H_2SO_4$ (5.29 g, 38.0 mmol) was suspended in $CH_2Cl_2$ (250 mL) and saturated $NaHCO_3$ solution (250 mL). Cyanoethoxycarbonyloxysuccinimide 1 (20.2 g, 95.3 mmol) was added and the reaction stirred for 2 h. The organic phase was separated. The aqueous phase was extracted with DCM (2×200 ml) and the combined organic phase was dried ($Na_2SO_4$), filtered and evaporated. The crude product was purified by flash chromatography with AcOEt/DCM (95:5) as eluant to afford 5 (3.78 g, 35%) as a white solid.

1H-NMR (200 MHz, $CDCl_3$): 11.80 (br s, 1H), 4.39 (q, 4H), 2.80 (t, 4H), 2.45 (s, 3H).

Example 6

Synthesis of N,N'-bis-benzoyl-2-methyl-2-thiopseudourea (6)

This compound was prepared as described by Derocque et al. (*Bulletin de la Société Chimique de France*, 1968, 5, 2062–2066).

Example 7

Synthesis of N,N'-bis-pivaloyl-2-methyl-2-thiopseudourea (7)

2-Methyl-2-thiopseudourea.½ $H_2SO_4$ (1.0 g, 3.60 mmole) was suspended in dry pyridine (14.4 ml). Pivaloylchloride (1.77 mL, 14.4 mmole) was added and the reaction mixture was stirred overnight. The reaction was quenched by addition of 5% aqueous $NaHCO_3$ solution (100 mL) and extracted with dichloromethane (2×50 mL). The organic phase was dried ($Na_2SO_4$), filtered and evaporated. The crude product was purified by flash column chromatography with EtOAc as eluant to afford 7 (1.27 g, 68%).

1H-NMR (200 MHz, DMSO-$d_6$): 13.10 (s, 1H), 2.39 (s, 3H), 1.22 (s, 18H); HRMS (FAB): Calcd for $C_{12}H_{23}N_2O_2S$- 259.480, Found: 259.1485.

Example 8

Synthesis of 2'-O-[(N,N'-bis-CEOC-guanidinium)ethyl]-5'-O-DMT-5-methyluridine (8)

Compound 5 (0.27 g, 0.95 mmole) was dissolved in anhydrous DMF (3 mL) at room temperature. To this, compound 4 (0.52 g, 0.86 mmole) and then triethylamine (0.12 ml, 0.86 mmole) was added, and the reaction was stirred at room temperature for 4 h. The reaction was quenched by addition of 5% $NaHCO_3$ solution (40 mL), extracted with EtOAc (2×60 mL) and the combined organic phases were dried ($Na_2SO_4$) filtered and evaporated. The crude product was purified by flash column chromatography with EtOAc as eluant to afford 8 (0.480 g, 66%).

1H NMR (200 MHz, $CDCl_3$): 11.70 (s, 1H), 8.60 (t, 1H), 8.51 (s, 1H), 7.66(s, 1H), 7.39–7.27 (m, 9H), 6.84 (d, 4H), 5.97 (d, 1H), 4.50–3.70 (m, 16H), 3.50 (m, 2H), 2.73 (m, 4H), 1.37 (s, 3H); $^{13}$C-NMR (80 MHz, $CDCl_3$): 164.50, 162.92, 158.70, 156.06, 153.02, 150.83, 144.43, 135.46, 135.29, 130.15, 128.06, 127.72, 127.18, 117.50, 116.88, 113.32, 111.09, 87.14, 86.82, 83.50, 82.40, 69.19, 68.94, 62.35, 61.09, 59.89, 55.29, 40.88, 18.05, 17.92, 11.87; HRMS (FAB): Calcd for $C_{42}H_{45}N_7O_{12}Na^+$ 862.3024, Found: 862.2991.

Example 9

Synthesis of 2'-O-[(N',N',-bis-CEOC-guanidinium)ethyl]-5'-O-DMT-5-methyluridine-3'-O-[(2-cyanoethyl)N,N-diisopropyl]Phosphoramidite (9)

Compound 8 (0.39 g, 0.46 mmol) and diisopropylamine tetrazolide (0.08 g, 0.46 mmol) were dried by coevaporation with anhydrous MeCN. The residue was redissolved in anhydrous MeCN (3 mL). 2-Cyanoethyl-N,N,N',N'-tetraisopropylphosphordiamidite (0.27 mL, 0.87 mmol) was added and the reaction mixture was stirred at room temperature, under argon, for 5 h. The solvent was evaporated and the crude product purified by flash chromatography with EtOAc/Hexanes as eluant to afford 9 (0.31 g, 64%).

31P NMR (80 MHz, $CDCl_3$): 150.87 and 150.78; HRMS (FAB): Calcd for $C_{51}H_{63}O_{13}N_9PCs$- 1172.3259, Found: 1172.3203.

Example 10

Synthesis of 2'-O-[2-(N,N'-bis-benzoyl-guanidinium)ethyl]-5'-O-DMT-5-methyluridine (10)

Compound 6 (0.5 g, 1.66 mmol) was dissolved in anhydrous DMF (3 mL). Nucleoside 4 (0.5 g, 0.83 mmol) and triethylamine (0.12 mL, 0.83 mmol) were added. The reaction mixture was stirred at room temperature for 5 h. The reaction mixture was added to brine (50 mL) and extracted with ethyl acetate (2×50 mL). The organic phase was dried over anhydrous $Na_2SO_4$ and evaporated to provide a yellow solid. The crude product was purified by flash column chromatography and eluted with ethyl acetate:hexane (1:1) to afford 10 (0.66 g, 93% yield).

1H NMR (200 MHz, $CDCl_3$): 14.50 (s, 1H), 9.79 (br s, 1H), 9.19 (s, 1H), 8.25 (d, 2H, J=6.62 Hz), 8.05 (d, 2H, J=6.94 Hz), 7.69 (s, 1H), 7.63–7.25 (m, 15H), 6.80 (d, 4H, J=8.8 Hz), 5.99 (S, 1H), 4.92 (m, 1H), 4.28 (m, 1H), 4.18–3.80 (m, 6H), 3.78 (s, 6H), 3.50 (m, 2H), 2.86 (d, 1H, J=9.01 Hz), 1.35 (s, 3H); $^{13}$C NMR (50 MHz, $CDCl_3$): 178.67, 168.43, 164.15, 158.73, 157.13, 150.56, 144.42, 135.49, 135.36, 135.12, 133.65, 132.11, 131.87, 130.17, 129.93, 129.51, 129.12, 128.06, 127.14, 113.32, 111.07, 87.85, 86.83, 83.19, 82.59, 68.96, 61.70, 55.26, 40.88, 11.89; HRMS (FAB): Calcd for $C_{48}H_{48}N_5O_{10}$- 854.340, Found: 854.3381.

Example 11

Synthesis of 2'-O-[2-(N,N'-bis-benzoyl-guanidinium)ethyl]-5-O-DMT-5-methyluridine-3'-O-[(2-cyanoethyl)N,N-diisopropyl]Phosphoramidite (11)

Compound 11 was prepared from compound 10, according to the procedure described in Example 9. Yield: 1.49 g (70%).

1H NMR (200 MHz, $CDCl_3$): 14.46 (s, 1H), 9.73 (br s, 1H), 8.64 (br s, 1H), 8.25 (d, 2H, J=6.63 Hz), 8.02 (d, 2H, J=6.94 Hz), 7.69 (s, 1H), 7.63–7.23 (m, 15H), 6.80 (d, 4H, J=8.74 Hz), 6.06 and 6.01 (2xd, 1H), 4.60–3.30 (m, 17H), 2.55 (t, 1H, J=7.6 Hz), 2.35 (t, 1H, J=7.5 Hz), 1.40–0.80 (m, 15H); $^{31}$P NMR (80 MHz, $CDCl_3$): 150.83 and 150.58; HRMS (FAB): Calcd for $C_{57}H_{64}N_7O_{11}PCS$- 1186.3456, Found: 1186.3410.

Example 12

Synthesis of 2'-O-[2-(N,N'-bis-pivaloylguanidinium)ethyl]-5'-O-DMT-5-methyl Uridine (12)

Compound 12 was prepared from compounds 4 and 7 according to the procedure described in Example 8. Yield: 0.98 g (73%).

1H NMR (200 MHz, $CDCl_3$): 13.39 (s, 1H), 9.50 (s, 1H) 9.40 (br s, 1H); 7.67 (s, 1H), 7.44–7.20 (m, 9H), 6.83 (d, 4H,

J=8.84 Hz), 5.95 (s, 1H), 4.50 (m, 1H), 4.20–4.00 (m, 2H), 3.90–3.60 (m, 4H), 3.78 (s, 6H), 3.55 (m, 2H), 2.78 (d, 1H, J=8.88 Hz), 1.37 (s, 3H), 1.26 (s, 9H), 1.18 (s, 9H); $^{13}$C NMR (50 MHz, CDCl$_3$): 193.82, 181.73, 164.12, 158.75, 156.57, 150.42, 144.39, 135.49, 135.34, 135.16, 130.17, 128.22, 128.04, 127.15, 113.32, 111.03, 87.76, 86.85, 83.17, 82.46, 68.94, 61.73, 60.42, 55.26, 42.01, 40.42, 27.90, 27.09, 11.87; HRMS (FAB): Calcd for $C_{44}H_{55}N_5O_{10}$- 814.4027, Found: 814.4054.

Example 13

Synthesis of 2'-O-[2-(N,N'-bis-pivaloylguanidinium) ethyl]-5'-O-DMT-5-methyluridine-3'-O-[(2-cyanoethyl)N,N-diisopropyl]Phosphoramidite (13)

Compound 13 was prepared from compound 12, as described in Example 9. Yield: 0.840 g (72%).

1H NMR (200 MHz, CDCl$_3$): 13.35 (s, 1H), 9.31 (s, 1H), 8.95 (br s, 1H), 7.72 and 7.65 (2×s, 1H), 7.45–7.20 (m, 9H), 6.86 (m, 4H), 6.00 and 5.95 (2×d, 1H), 4.60–3.20 (m, 17H), 2.63 (t, 1H, J=7.72 Hz), 2.37 (t, 1H, J=7.2 Hz), 1.40–0.80 (m, 33H); $^{31}$P NMR (80 MHz, CDCl$_3$): 150.73 and 150.55; HRMS (FAB): Calcd for $C_{53}H_{72}N_7O_{11}PCs$- 1146.4082, Found: 1146.4034.

Example 14

Synthesis of 5-O-DMT-2'-O-[2-methoxyethyl]-5-(3-aminoprop-1-yne) Uridine (14)

2'-O-Methoxyethyluridine (synthesized according to the procedures described in U.S. Pat. No. 5,760,202) was treated with an excess of pyridine/benzoyl chloride to give 3',5'-dibenzoyl-2'-O-methoxyethyl uridine in quantitative yield. This compound was treated with lithium iodide (1 equivalent) and ceric ammonium nitrate (3 equivalents) in acetonitrile as the solvent. After stirring overnight, TLC indicated the formation of 5-iodo-3'-5'-dibenzoyl-2'-O-methoxyethyl-uridine. Acetonitrile was evaporated and the residue redissolved in CH$_2$Cl$_2$ and extracted with saturated NaHCO$_3$ solution. The organic layer was dried (Na$_2$SO$_4$) and evaporated to dryness. The residue was purified on a silica column and eluted with EtOAc/Hexane (7:3). Fractions containing the product were pooled together and concentrated. N-Trifluoro-acetylpropargylamine (3 equivalents) was been added, to this compound along with tetrakis(triphylphosphine) palladium(0) [(Ph$_3$P)$_4$ Pd], copper iodide, triethylamine and DMF to provide the C-5-(N-trifluoroacetyl)-propargylamine derivative. Treatment of this compound with sodium in methanol afforded the 3'-5'-bis-hydroxyl parent compound. This compound was 5'-dimethoxy tritylated. The trifluoroacetyl group was deprotected by treatment with NH$_4$OH/pyridine.

Example 15

Synthesis of 5'-O-DMT-2'-O'[2-(methoxy)ethyl]-5-[3-(N,N'-bis-CEOC-guanidinium)prop-1-yne] Uridine (15)

Compound 15 was prepared from compounds 5 and 14, according to the procedure described in Example 8. Yield: 0.54 g (17%).

1H NMR (200 MHz, CDCl$_3$): 11.61 (s, 1H), 9.80 (br s, 1H), 8.13 (d, 2H), 7.45–7.20 (m, 9H), 6.83 (d, 4H, J=8.82 Hz), 5.93 (d, 1H, J=3.48 Hz), 4.45 (br s, 1H), 4.16–3.96 (m, 6H), 3.77 (s, 6H), 3.82–3.39 (m, 6H), 3.37 (s, 3H), 2.73 (q, 4H, J=6.3 Hz); $^{13}$C NMR (50 MHz, CDCl$_3$): 162.07, 161.77, 158.53, 155.03, 152.67, 149.60, 149.39, 144.64, 143.22, 136.25, 135.62, 135.40, 130.03, 128.08, 127.90, 126.88, 123.77, 117.07, 116.20, 113.38, 99.27, 88.05, 86.96, 83.97, 83.12, 74.84, 71.84, 70.39, 62.35, 60.86, 60.44, 60.08, 59.02, 55.32, 31.71, 18.1.

Example 16

Synthesis of 5'-O-DMT-2'-O'-[2-(methoxy)ethyl]-5-[3-(N,N'-bis-CEOC-guanidinium)prop-1-yne] uridine-3'-O-[(2-cyanoethyl)N,N-diisopropyl] phosphoramidite (16)

Compound 16 was prepared from compound 15, according to the procedure described in Example 9. Yield: 0.24 g (35%).

31P NMR (80 MHz, CDCl$_3$): 150.91 and 150.15; HRMS (FAB): Calcd for $C_{54}H_{64}O_{14}N_9PNa$- 1116.4208, Found: 1116.4243.

Example 17

Synthesis of 5'-O-DMT-2'-O'[2-(methoxy)ethyl]-5-[3-(N,N'-bis-benzoylguanidinium)prop-1-yne] uridine (17)

Compound 17 was prepared from compounds 6 and 14, according to the procedure described in Example 8. Yield: 0.86 g (38%).

1H NMR (200 MHz, CDCl$_3$): 14.34 (s, 1H), 9.57 (br s, 1H), 9.29 (t, 1H, J=4.88 Hz), 8.24 (d, 2H, J=6.62 Hz), 8.20 (s, 1H), 8.02 (d, 2H, J=6.72 Hz), 7.63–7.19 (m, 15H), 6.82 (d, 4H, J=8.84 Hz), 5.95 (d, 1H, J=3.3 Hz), 4.47 (br s, 1H), 4.26–4.00 (m, 5H), 3.84–3.37 (m, 14H), 2.10 (br s, 1H); $^{13}$C NMR (50 M Hz, CDCl$_3$): 178.62, 167.83, 161.65, 158.60, 156.06, 149.43, 144.72, 140.75, 137.41, 135.60, 135.37, 133.55, 132.12, 131.93, 130.05, 129.65, 129.10, 128.00, 126.88, 113.35, 99.66, 88.71, 88.11, 86.95, 83.93, 83.08, 74.54, 71.37, 70.32, 69.06, 62.28, 58.96, 55.19, 31.62; HRMS (FAB): Calcd for $C_{51}H_{49}O_{11}N_5$- 908.3507, Found: 908.3546.

Example 18

Synthesis of 5'-O-DMT-2'-O-[2-(methoxy)ethyl]-5-[3-(N,N'-bis-benzoylguanidinium)prop-1-yne] uridine-3'-O-[(2-cyanoethyl)N,N-diisopropyl] phosphoramidite (18)

Compound 18 was prepared from compound 17, according to the procedure described in Example 9. Yield: 0.72 g (86%).

31PNMR (80 MHz, CDCl$_3$): 150.93 and 150.21; HRMS (FAB): Calcd for $C_{60}H_{66}N_7O_{12}P$- 1108.4585, Found: 1108.4548.

Example 19

Synthesis of 5-(3-phthalimidopropy-1-nyl)-2'-deoxyuridine (19)

To a suspension of 5-iodo-2'-deoxyuridine (2 mmol) in 10 mL of CH$_2$Cl$_1$, is added trifluoroacetic anhydride (5 mmol) at room temperature. The mixture is stirred overnight. After concentration of the mixture, the mixture is dried in vacuo at room temperature to give a solid foam of 3',5'-di-O-trifluoroacetyl-5-iodo-2'-deoxyuridine. To a mixture of 3',5'-di-O-trifluoroacetyl-5-iodo-2'-deoxyuridine (5 mmol) and N-1-phthalimidoprop-1-yne (10 mmol), tetrakis (triphenylphosphine) palladium(0) (0.2 mmol), copper(I) iodide (0.3 mmol) and triethylamine (6 mmol) are added in 10 ml DMF. The mixture is stirred at room temperature for 18 hours and then concentrated in vacuo. To the concentrate, AG-1×8 anion exchange resin ($HCO_3^-$ form, 3 equivalents), 20 mL of methanol and 20 mL of $CH_2Cl_2$ are added and the suspension is stirred for 1 h. The residue is purified by silica column chromatography to afford 5-(3-phthalimidoprop-1-ynyl)-2'-deoxyuridine (19).

Example 20

Synthesis of 5'-O-DMT-5-(3-phthalimidoprop-1-nyl)-2'-deoxy-uridine (20)

5-(3-Phthalimidoprop-1-nyl)-2'-deoxyuridine (19) is treated with 1.2 equivalents of 4,4'-dimethoxytrityl chloride in pyridine containing 0.1 equivalent of dimethylaminopyridine. After stirring for 4 h, pyridine is evaporated and the residue dissolved in methylene chloride, washed with saturated sodium bicarbonate solution, dried over anhydrous sodium sulfate and concentrated. The residue is purified using silica column chromatography using ethyl acetate-:hexanes to yield the 5'-O-DMT derivative (20).

Example 21

Synthesis of 5'-O-DMT-2'-deoxy-5-[3-(amino)prop-1-yne]uridine (21)

The above phthalimido compound (20), on hydrazine treatment, yielded amino compound 21 according to the procedure described in Example 4.

Example 22

Synthesis of 5'-O-DMT-2'-deoxy-5-[3-(N,N'-bis-CEOCguanidinium)-prop-1-yne]uridine (22)

Compound 22 was prepared from compound 21 according to the procedure described in Example 8. Yield: 3.47 g (63%).

1H NMR (200 MHz, $CDCl_3$): 11.59 (s, 1H), 9.80 (br s, 1H), 8.22 (br s, 1H), 8.11 (s, 1H), 7.43–7.20 (m, 9H), 6.82 (d, 4H, J=8.68 Hz), 6.28 (t, 1H, J=6.15 Hz), 4.50 (br s, 1H), 4.29 (m, 4H), 4.11 (m, 3H), 3.75 (s, 6H), 3.40 (m, 3H), 2.69 (m, 4H), 2.50 (m, 1H), 2.30 (m, 1H); $^{13}$C NMR (50 MHz, $CDCl_3$): 162.92, 162.24, 158.82, 155.41, 152.88, 149.60, 144.89, 143.87, 135.79, 135.68, 130.28, 128.26, 127.20, 117.43, 116.64, 113.54, 99.40, 88.27, 87.20, 86.88, 86.08, 75.17, 72.28, 63.83, 61.09, 60.29, 55.54, 41.75, 31.99, 18.30, 18.11; HRMS (FAB): Calcd for $C_{42}H_{42}N_7O_{11}$- 820.2942, Found: 820.2918.

Example 23

Synthesis of 5'-O-DMT-2'-deoxy-5-[3-(N,N'-bis-CEOCguanidinium)-prop-1-yne]uridine-3'-O-[(2-cyanoethyl)N,N-diisopropyl]phosphoramidite (23)

Compound 23 was prepared from compound 22 according to the procedure described in Example 9. Yield: 1.43 g (58%).

31P NMR (80 MHz, $CDCl_3$): 149.56 and 149.26; HRMS (FAB): Calcd for $C_{51}H_{58}N_9O_{12}PNa$- 1042.3840, Found: 1042.3808.

Example 24

Synthesis of 5'-O-DMT-2'-O-[2-(N-,N'-CEOC-guanidinium)ethyl]-3-O-succinyl-5-methyluridine (24)

Compound 8 (0.252 g, 0.30 mmol) was co-evaporated with anhydrous acetonitrile. To this, succinic anhydride (0.6 g, 0.6 mmol), DMAP (0.018 g, 0.15 mmol), anhydrous pyridine (0.048 mL, 0.6 mmol) and $CH_2Cl_2$ (1 mL) were added and stirred at room temperature under an inert atmosphere for 4 h. The reaction mixture was diluted with $CH_2Cl_2$ (25 mL) and washed with cold 10% aqueous citric acid (20 mL) and brine (25 mL). The organic phase was dried over anhydrous $Na_2SO_4$ and concentrated to provide compound 22 (0.248 g, 88%) as a foam. $R_f$(0.25, 5% MeOH in $CH_2Cl_2$).

1H NMR (200 MHz, $CDCl_3$): 1.34 (s, 3H), 2.2–2.5 (m, 8H), 3.45 (d, 1H, J=5.4 Hz), 3.64 (d, 1H, J=11.62 Hz), 3.72–4 (m, 10H), 4.15 (br s, 1H), 4.26–4.38 (m, 6H), 5.40 (d, 1H, J=4.4 Hz), 5.93 (d, 1H, J=2.12 Hz), 6.83 (d, 4H, J=7.22 Hz), 7.24–7.4 (m, 9H), 7.77 (s, 1H), 8.57 (s, 1H), 10.51 (s, 1H); HRMS (FAB): Calcd for $C_{46}H_{50}N_7O_{15}$ 940.3365, Found: 940.3346.

Example 25

Synthesis of 5'-O-DMT-2'-O-[2-(N,N'-CEOC-guanidinium)ethyl]-5-methyluridine-3'-O-succinyl-CPG (25)

Compound 24 (0.227 g, 0.24 mmol) was dried over $P_2O_5$ in vacuo at 40° C. overnight. Anhydrous DMF (0.62 mL) was added followed by 2-(1H-benzotriazole)-1-yl)-1,1,3,3-tetramethyluroniumtetrafluoroborate (0.077 g, 0.24 mmol) and N-methylmorpholine (53 mL, 0.48 mmol). The reaction mixture was vortexed to obtain a clear solution. To this solution, anhydrous DMF (2.38 mL) and activated CPG (1.03 g, 115.2 mmol/g, particle size 120/200, mean pore diameter 520 Å) were added. The reaction mixture was then allowed to shake on a shaker for 18 h. An aliquot was withdrawn and the loading capacity was estimated. Functionalized CPG was filtered and washed thoroughly with DMF, $CH_3CN$ and $Et_2O$. It was then dried in vacuo overnight. Functionalized CPG (23) was then suspended in a capping solution (acetic anhydride/lutidine/N-methylimidazole in THF, PerSeptive Biosystems, Inc.) and allowed to shake on a shaker for 2 h. Functionalized CPG was then filtered, washed with $CH_3CN$ and $Et_2O$, dried in vacuo and the loading capacity determined by standard procedure. Final loading was 32.8 mol/g.

Example 26

Synthesis of oligonucleotides containing 2'-O-[2-(guanidinium)-ethyl] Modification and Deprotection of CEOC Group using a Novel Procedure The amidite 9 was dissolved in anhydrous acetonitrile to obtain a 0.1 M solution and loaded onto a Expedite Nucleic Acid Synthesis system (Millipore 8909) to synthesize the oligonucleotides. The coupling efficiencies were more than 98%. For the coupling of the modified amidite (9) coupling time was extended to 10 minutes and this step was carried out twice. All other steps in the protocol supplied by Millipore were used as such. After completion of the synthesis, CPG was suspended in 50% piperidine in water and kept at room temperature for 24 h to deprotect the CEOC protecting group on the guanidino group. Under the same conditions, oligonucleotides are cleaved from CPG. The solvent was then evaporated and the CPG treated with aqueous ammonia solution (30 wt %) at 55° C. for 6 h to complete the deprotection of exocyclic amino protecting groups. This was purified on High Performance Liquid Chromatography (HPLC, Waters, C-4, 7.8×300 mm, A=50 mM triethylammonium acetate, pH=7, B=acetonitrile, 5 to 60% B in 55 Min, Flow 2.5 mL/min.=260 nm). Detrytilation with aqueous 80% acetic acid and evaporation, followed by desalting by HPLC on Waters C-4 column, gave 2'-modified oligonucleotides (Table I). Oligonucleotides were analyzed by HPLC, CGE and mass spectrometry.

TABLE I

Oligonucleotides containing 2'-O-[2-(guanidinium) ethyl modification

| SEQ ID No. | Sequence (5'—3') | Mass Calculated | Mass Observed | HPLC Ret. Time (min[a]) |
|---|---|---|---|---|
| 1 | T*CC AGG T*GT* CCG CAT* C | 5238.22 | 5238.21 | 18.69 |
| 2 | CTC GTA CT*T* T*T*C CGG TCC | 5797.49 | 5797.15 | 18.06 |
| 3 | TTT TTT TTT TTT TTT T*T*T* T* | 6122.93 | 6122.60 | 18.21 |
| 13 | TTT TTT TTT TTT TTT TT*T T* | 5920.59 | 5920.21 | 19.32 |
| 7 | TTT TTT TTT TTT TTT TTT T* | 5818.47 | 5818.62 | 19.46 |
| 8 | T*T*T* T*T*C TCT CTC TCT | 4931.41 | 4931.46 | 21.93 |
| 9 | TT*T TT*C TCT* CTC T*CT | 4830.8 | 4830.29 | 16.07 |
| 10 | T*TT* TT*C TCT CTC TCT | 4729.73 | 4729.47 | 19.11 |

Ret. time = retention time (in minutes);
T* = 2'-O-[2-(guanidinium)ethyl] $^{5Me}$U
[a]Waters C-4, 3.9 × 300 mm, solvent A = 50 mm TEAAc, pH 7; Solvent B = CH$_3$CN; gradient 5–60% B in 55 min; flow rate 1.5 mL/min., l = 260 nm

TABLE II

Tm values of 2'-O-[2-(2-guanidiniumethyl) oxyethyl] modifications

| SEQ ID No. | Sequence 5'—3' | Target RNA °C. | ΔTm °C. | ΔTm/mod. |
|---|---|---|---|---|
| 11 | TCC AGG TGT CCG CAT C | 62.3 | — | |
| 1 | T*CC AGG T*GT* CCG CAT* C | 70.5 | 8.2 | 2.05 |
| 12 | CTC GTA CTT TTC CGG TCC | 61.8 | | |
| 2 | CTC GTA CT*T* T*T*C CGG TCC | 61.28 | -0.53 | -0.13 |

Figure 2:
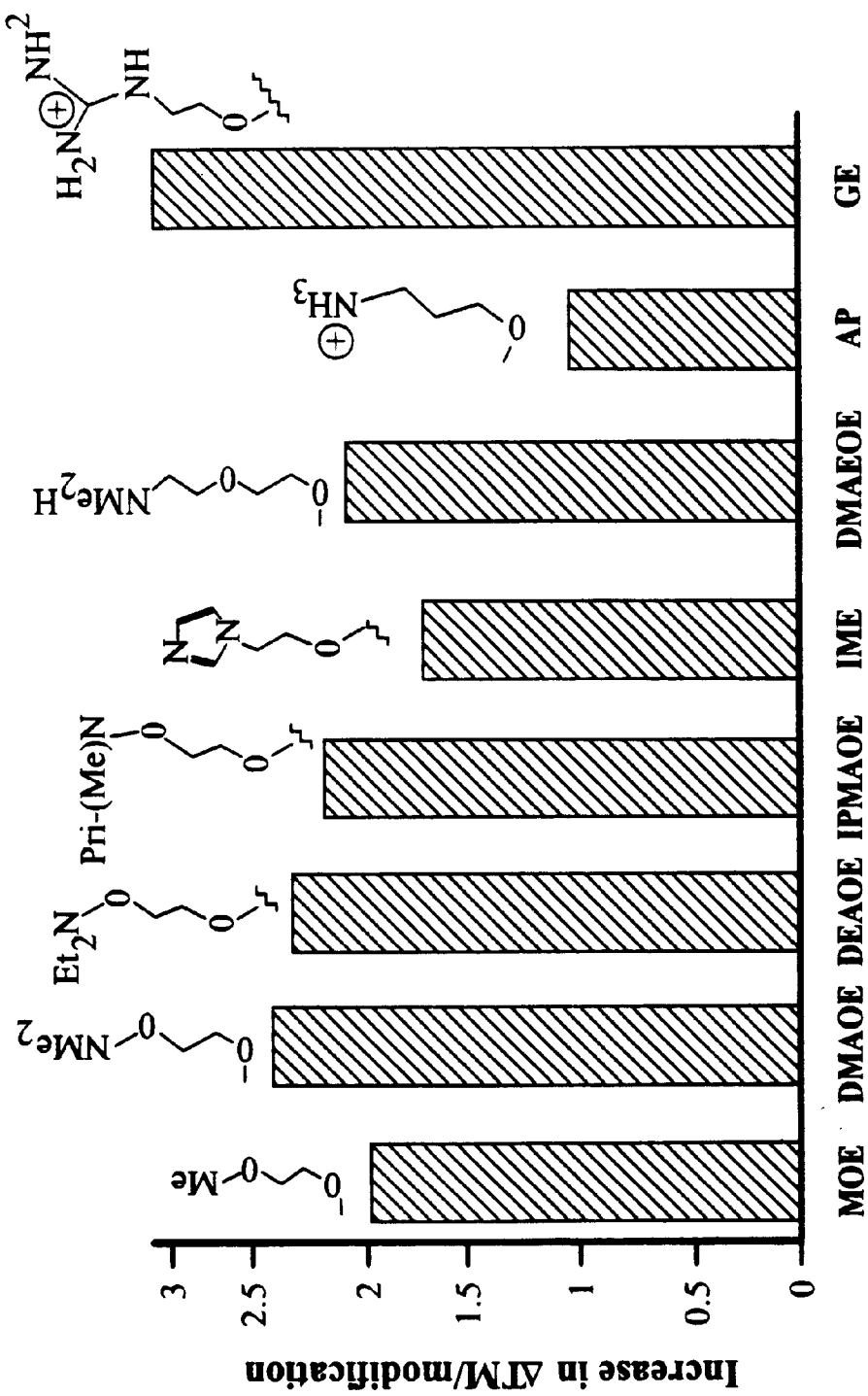
FIG. 2 shows the binding affinity/modification of 2'-O-[2-(guanidinium)ethyl] modification in comparison to other known 2'-modifications such as 2'-O-MOE (methoxyethyl), 2'-O-DMAOE (dimethylaminooxyethyl), 2'-O-DEAOE (diethylaminooxyethyl), 2'-O-IPMAOE (isopropylmethylaminooxyethyl), 2'-O-imidazoylethyl (IE) and 2'-aminopropyl (AP).

T* = 2'-O-[2-(guanidinium)ethyl $^{5Me}$U.
The ΔTm/modification relative to 2'-deoxy P = S is obtained by adding 0.8 to the value shown in last column. This value relative to other modifications is shown in FIGS. 2 and 3.

2'-O-Guanidiniumethyl modification shows the highest binding affinity change (ΔTm/mod.) among 2'-modifications studied so far. This point is illustrated in FIG. 2.

Figure 3:
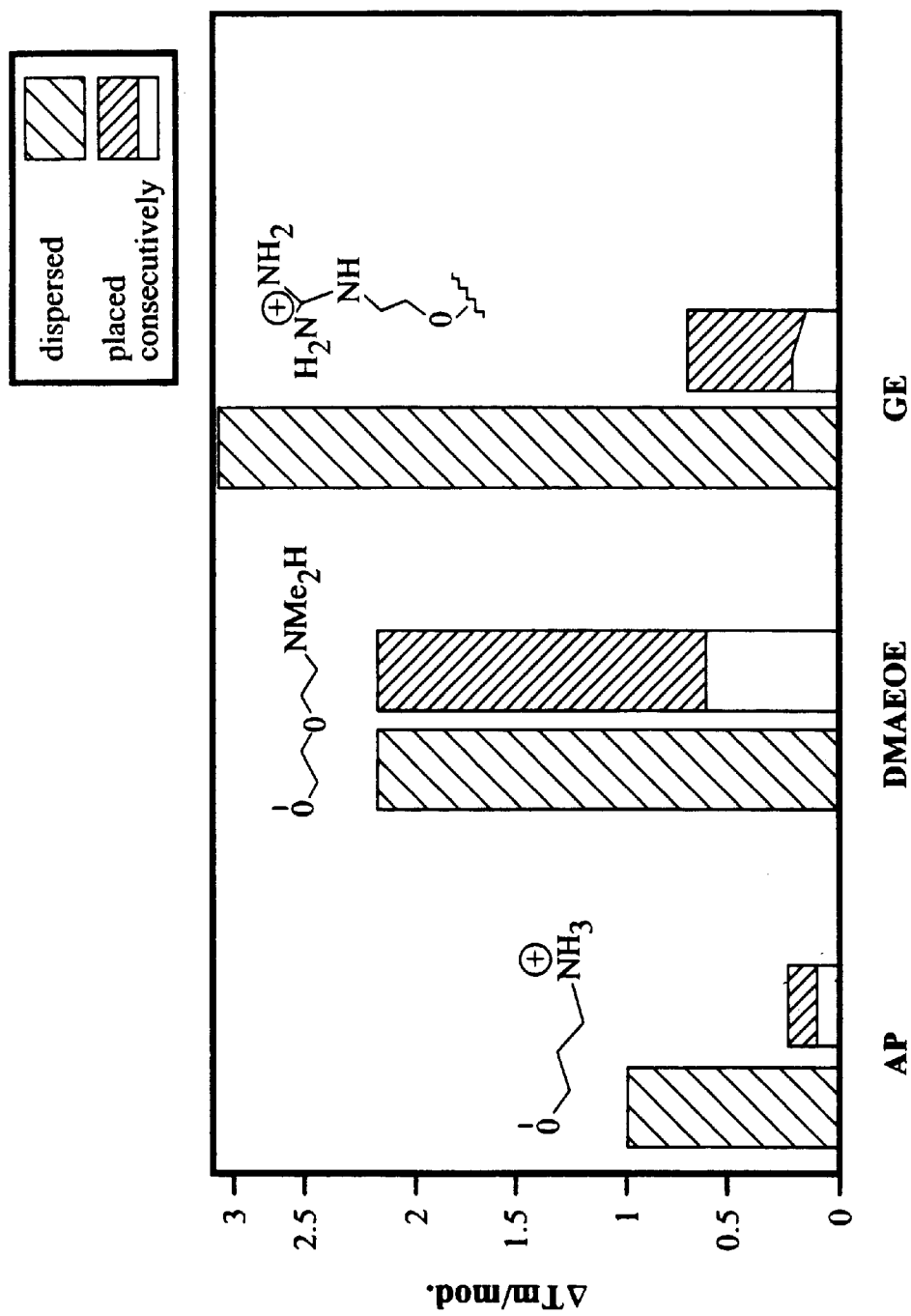
FIG. 3 shows binding affinity of 2'-O-[2-(guanidinium)ethyl] modified oligonucleotides as a function of position in placement compared to 2'-aminopropyl and 2'-O-DMAEOE (dimethylaminoethyloxyethyl).

As shown in FIG. 3, the ΔTm/modification depends on the nature of placement of the cationic modification. There could be charge repulsion when the cationic groups are placed close to each other.

Example 27

Synthesis of N'-Benzoyl-2'-deoxy-5'-O-(4,4'-dimethoxytrityl)-cytidine (26)

2'-Deoxycytidine (5.82 g, 25.6 mmol) was dried by evaporation and taken up in dry pyridine (100 mL). To this suspension, trimethylsilyl chloride (11.5 mL, 90.6 mmol) was added and the mixture was stirred at ambient temperature for 2 h. The reaction mixture was cooled in an ice-water bath and benzoyl chloride (4.60 mL, 39.6 mmol) was slowly introduced. The ice-waterbath was removed and the mixture was stirred at room temperature for additional 2 h. The reaction was quenched by adding methanol (15 mL), concentrated to one half of the original volume and filtered. To the filtrate, water (30 mL) was added and the solution was evaporated to an oil. Further evaporation with water (3×30 mL) was performed to remove pyridine, and the resulting residue was partitioned between water and ethyl acetate. After vigorous stirring, the product crystallized from the aqueous layer. The product crystals were washed with cold water and ethyl acetate and were used in the next step without further purification. Crude N$^4$-benzoyl-2'-deoxycytidine was dried by evaporation with dry pyridine (3×50 mL) and then dissolved in the same solvent (100 mL). 4,4-Dimethoxytritylchloride (7.4 g, 22 mmol) was added portion-wise to the reaction mixture and the stirring was continued overnight at ambient temperature. The reaction mixture was evaporated to afford an oil and dissolved in dichloromethane (100 mL). The organic phase was washed with saturated aqueous NaHCO$_3$ (50 mL) and water (3×100 mL) and dried with anhydrous Na$_2$SO$_4$. After coevaporation with toluene, the residue was applied onto a silica gel column and eluted with a gradient of MeOH in CH$_2$Cl$_2$ (0–8% MeOH). The product (25) was obtained in 65% yield (9.0 g) starting from 2'-deoxycytidine.

1H NMR (200 MHz, CDCl$_3$): 8.30 (s, 1H, d, J=7.6), 7.45–7.10 (m, 9H), 6.84 (m, 4H), 7.90–7.40 (m, 5H), 6.31 (t, 1H, J=5.9, Hz), 4.55 (m, 1H), 4.19 (m, 1H), 3.78 (s, 6H), 3.49 (dd, 1H, J=3.2 and 11.0 Hz), 3.42 (dd, 1H, J=3.9 and 10.8 Hz), 2.77 (m, 1H).

Example 28

Synthesis of 2'-deoxy-N'-[2-(amino)ethyl]-5'-O-(4,4'-dimethoxy-trityl)cytidine (27)

A solution of ethylenediamine (96.9 mmol) in 2-propanol (10 mL) is added to compound 25 (2.61 g, 4.12 mmol) and stirred until the mixture is clear. 1,5,7-Triazabicyclo[4.4.0]dec-5-ene (TBD, 2.40 g, 17.2 mmol) is added and the reaction mixture is stirred at ambient temperature for 48 h. The reaction mixture is evaporated to afford an oil, dissolved in CHCl$_3$ (100 mL), extracted with 0.1 mol L$^{-1}$ aq. NaOH (2×50 mL) and water (4×50 mL). The organic phase is dried with anhydrous Na$_2$SO$_4$, evaporated and dissolved in CH$_2$Cl$_2$. Silica gel column purification yields the pure product 27.

Example 29

Synthesis of 2'-deoxy-5'-O-(4,4'-dimethoxytrityl-N'-[2-(N,N'-bis-CEOC-guanidinium)ethyl]cytidine (28)

Compound 27, on treatment with reagent 5, gives compound 28 as described in Example 8.

Example 30

Synthesis of 2'-deoxy-5'-O-(4,4'-dimethoxytrityl)-N'-[2-(N,N'-bis-CEOC-guanidinium)ethyl]cytidine-3'-O-[(2-cyanoethyl)N,N-diisopropyl) Phosphoramidite (29)

Compound 29 (0.29 mmol) is dried by evaporation with dry acetonitrile (3–20 mL) and finally in vacuo for 30 minutes. 2-Cyanoethyl-N,N,N',N'-tetraisopropylphosphorodiamidite (0.12 mL, 0.38 mmol) and dry acetonitrile (1.0 mL) are added and the mixture is stirred until all material dissolves. 1H-Tetrazole (0.45 mol L$^{-1}$ in MeCN, 0.64 mL, 0.29 mmol) is added and the reaction mixture is shaken. After one hour at ambient temperature, 100 mL of saturated aqueous NaHCO$_3$ solution is added to the reaction mixture and the resulting solution is extracted with ethyl acetate (2×40 mL). The organic phase is dried with anhydrous Na$_2$SO$_4$ and evaporated to dryness to afford pure compound 29.

Example 31

Synthesis of 5'-O-(4,4'-dimethoxytrityl)-5-(3-aminoprop-1-nyl)-N4-benzoyl-2'-deoxycytidine (33)

To 5-iodo-2'-deoxycytidine (5 mmol), tetrakis(triphenylphosphine) palladium(0) (0.5 mmol), copper(I) iodide (1 mmol) and N-1-phthalimidoprop-3-yne (12 mmol) in 15 mL of dry DMF, 10 mmol of triethylamine is added. After stirring for 18 h, AG-1×8 anion exchange resin (HCO$_3^-$ form, 3 equivalents), 20 mL of methanol, and 20 mL of CH$_2$Cl$_2$ are added, and the suspension is stirred for 1 h. The reaction is filtered through a sintered glass funnel, and the DMF removed in vacuo. Flash chromatography yielded the product (30). This compound is treated with benzoic anhydride (one equivalent) in dry pyridine to give N$^4$-benzoyl derivative (31). To a mixture of N$^4$-benzoyl derivative and 4,4'-dimethoxytritylchloride, dry pyridine is added to afford the 5'-dimethoxytrityl derivative (32), which is then converted into amino compound 33 according to the procedure described in Example 4.

Example 32

Synthesis of 5'-O-(4,4'-dimethoxytrityl)-2-[2-(N,N'-bis-CEOCguanidinium)ethyl]amino-2'-deoxyadenosine-3'-O-[(2-cyanoethyl)N,N-diisopropyl]phosphoramidite (34)

2-Fluoroadenosine is synthesized according to the procedure described by Krolikiewicz and Vorbruggen (Nucleosides & Nucleotides 13, 673, 1994). Ethylenediamine (5 equivalents in 2-methoxyethanol) is added to 2-fluoroadenosine and heated at 100°. The resulting 2-(aminoethyl) derivative is then converted into 2-(2-guanidinium)ethyl derivative with reagent 5 as described in example 8. This was then treated with benzoyl chloride under transient protection conditions and then dimethoxytritylated at the 5'-position. The resulting compound was then phosphitylated following the procedures described above to give the adenosine derivative 36 functionalized at the 2-position.

Example 33

Synthesis of 5'-O-(4,4'-dimethoxytrityl)-2-[2-(bis-N,N-CEOCguanidinium)ethyl]-2'-deoxyguanosine-3'-O-[(2-cyanoethyl)N,N-diisopropyl] phosphoramidite (34)

2-Fluoroinosine is synthesized according to the procedure described by Krolikiewicz and Vorbruggen (Nucleosides & Nucleotides 13, 673, 1994). Ethylenediamine (5 equivalents in 2-methoxyethanol) is added to 2-fluoroinosine and heated at 100° C. The free amine is guanylated on the side chain at the 2-position by treatment with reagent 5 as described in Example 8. The product is first dimethoxytritylated at the 5'-position, then phosphitylated following the procedures described above to give the guanosine derivative functionalized at the 2-position (37).

Example 34

Synthesis of 5'-O-(4,4'-dimethoxytrityl)-N$^2$-isobutyryl-N$^6$-[2-(bis-N,N'-CEOC-guanidinium)ethyl]-2-aminoadenosine-3'-O-[(2-cyanoethyl)N,N-diisopropyl]phosphoramidite (35)

To 2'-deoxyguanosine (2 mmol), dried by coevaporation with pyridine, suspended in 40 mL of pyridine and cooled in an ice bath under an argon atmosphere, trifluoroacetic anhydride (16 mmol) is added following the procedure of Kung and Jones (Tetraheron Lett., 32, 3919, 1991). After 40 minutes, ethylenediamine (30 mmol) is added and stirred for 24 h at room temperature. The reaction mixture is concentrated and purified by silica column chromatography. The product is guanylated with reagent 5 as in Example 8 and protected at N$^2$-position with an isobutyryl group by treating with isobutyric anhydride, 5'-dimethoxytritylated at the 5'-position and purified. The resulting compound is treated with benzoic anhydride (N$^6$ protection) and then phosphitylated following the procedures described above to afford the 2,6-diaminopurine derivative functionalized at the 6-position (35).

Example 35

Nuclease Stability Assay of 2'-O-[2-(guanidinium)ethyl] oligonucleotides (SEQ ID No. 3: ISIS 109990, ISIS 109989 and ISIS 109973)

Figure 4:
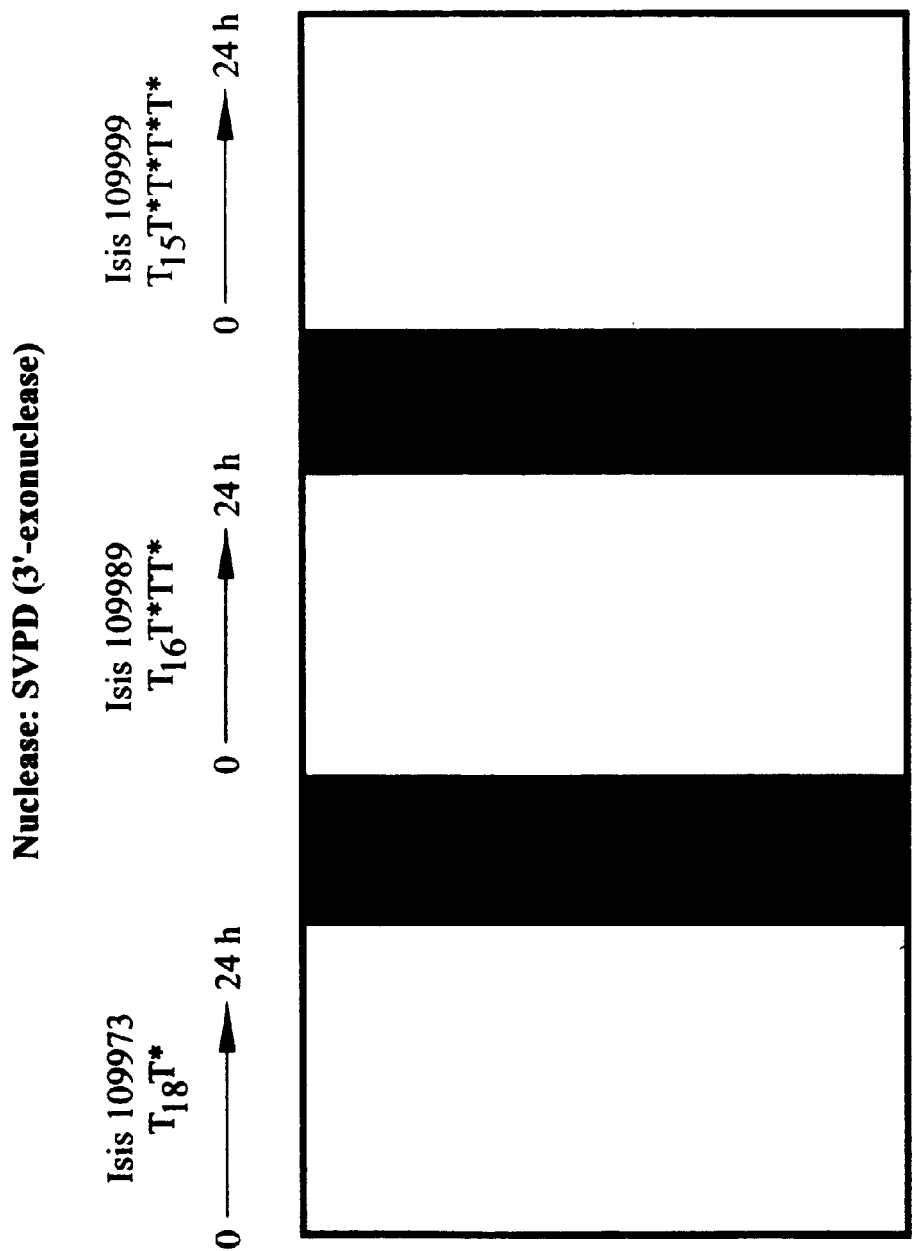
FIG. 4 shows electropherograms demonstrating the nuclease resistance of 2'-o-[2-(guanidinium)ethyl] modified oligonucleotides.
Figure 5:
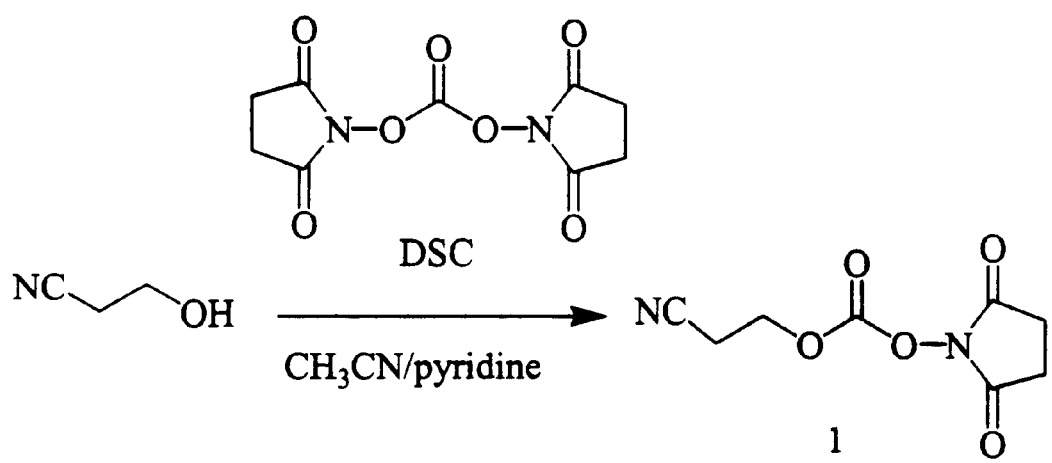
FIG. 5 shows the synthesis of compound 1.
Figure 6:
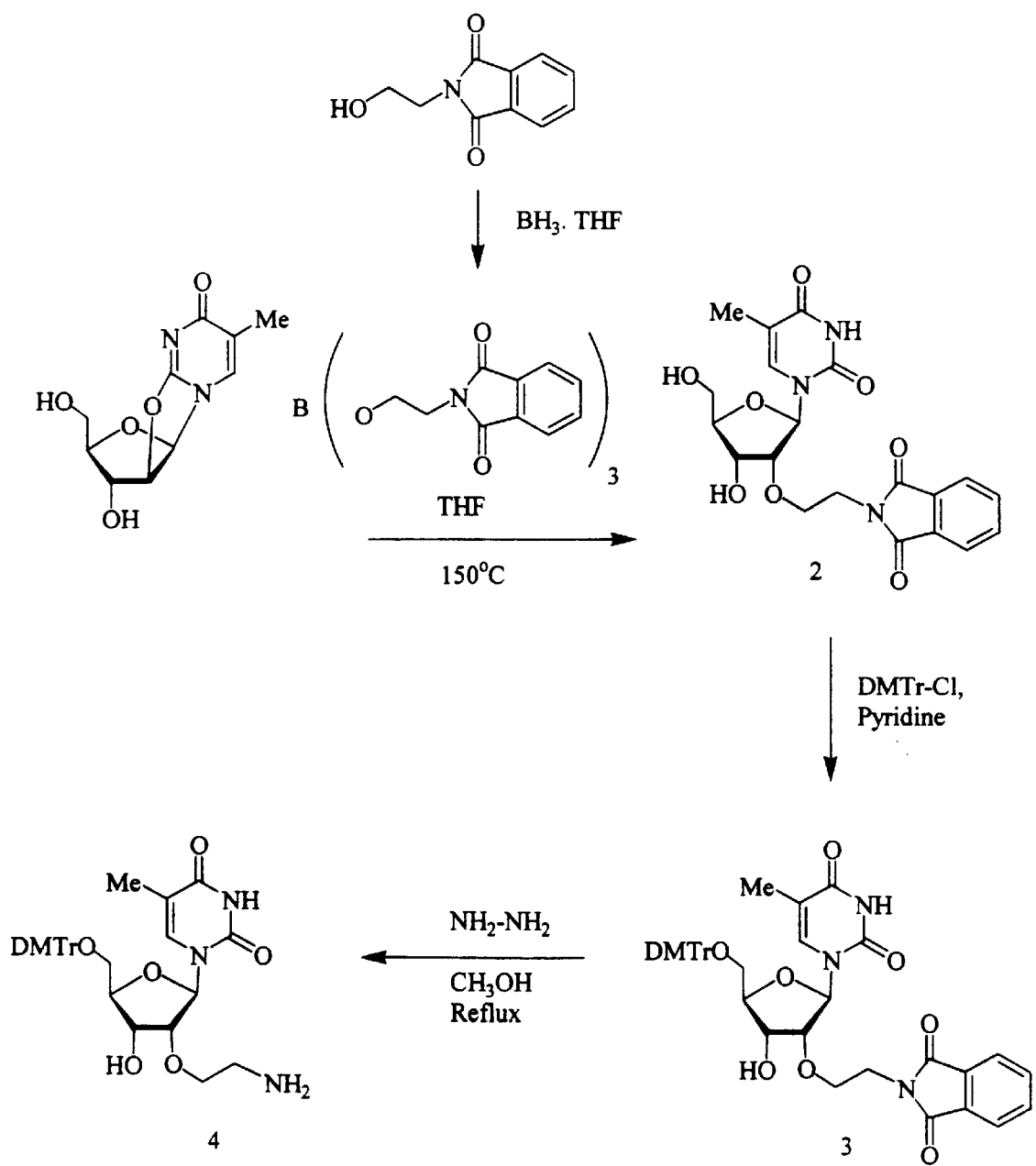
FIG. 6 shows the synthesis of compound 4.
Figure 7:
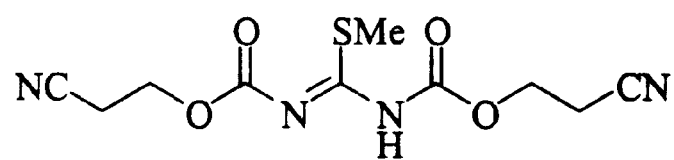
FIG. 7 shows the structures of compounds 5–7.
Figure 7:
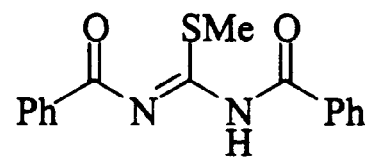
Figure 7:
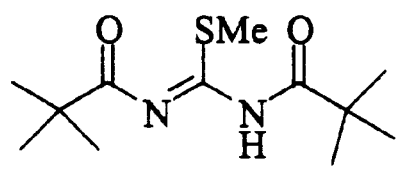
Figure 8:
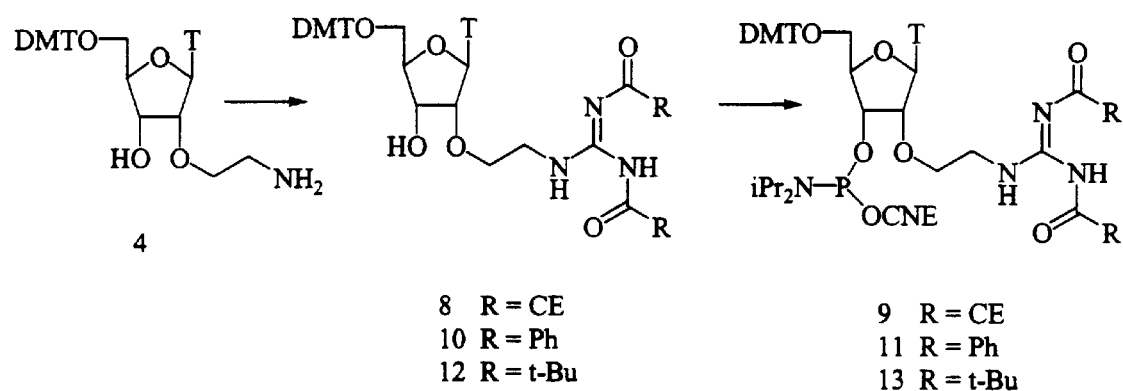
FIG. 8 shows the synthesis of compounds 8–13.
Figure 9:
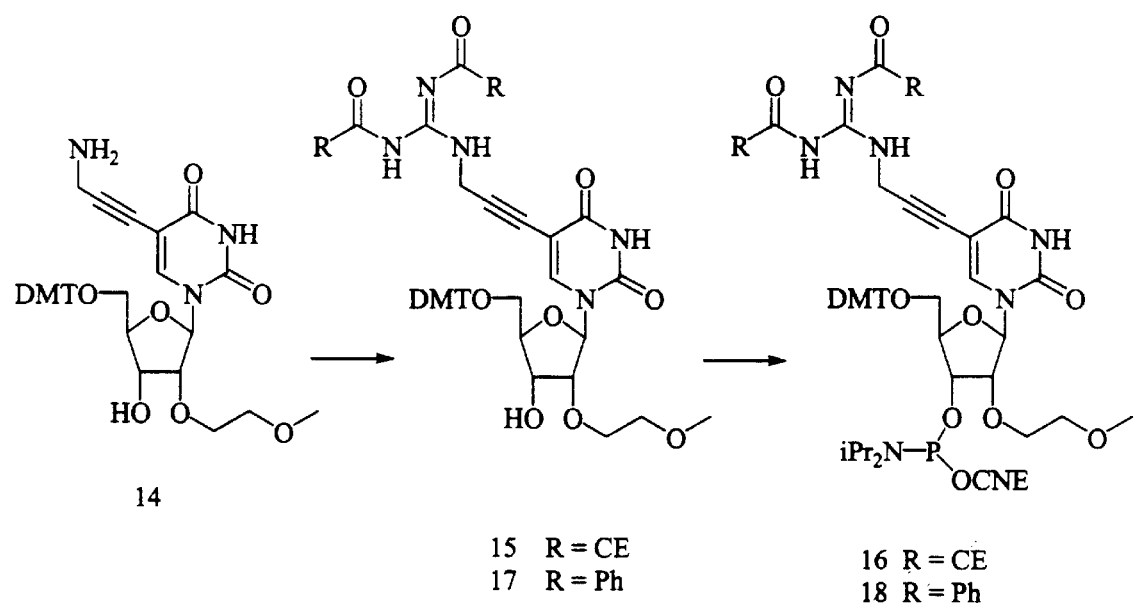
FIG. 9 shows the synthesis of compounds 15–18.
Figure 10:
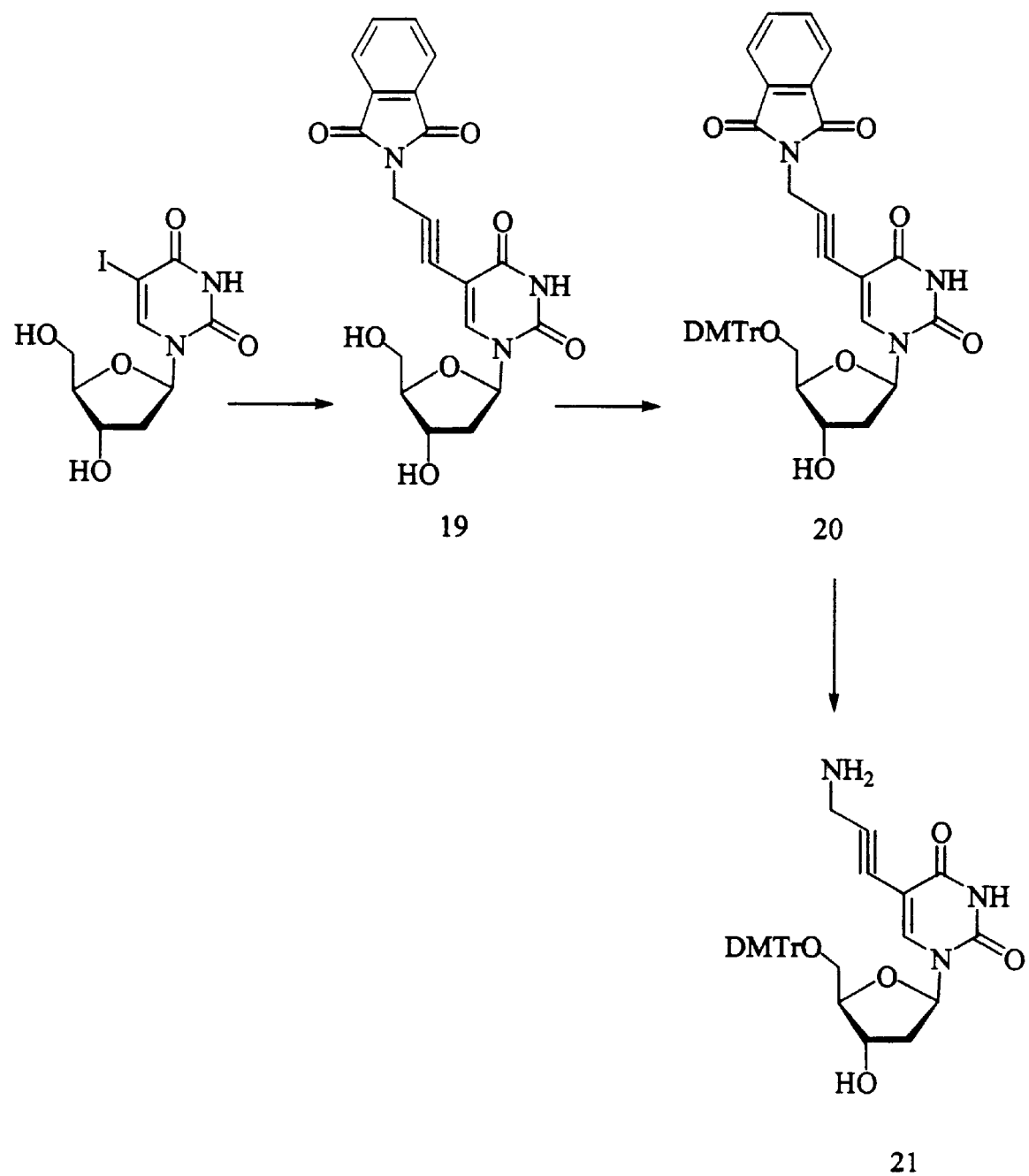
FIG. 10 shows the synthesis of compounds 20–21.
Figure 11:
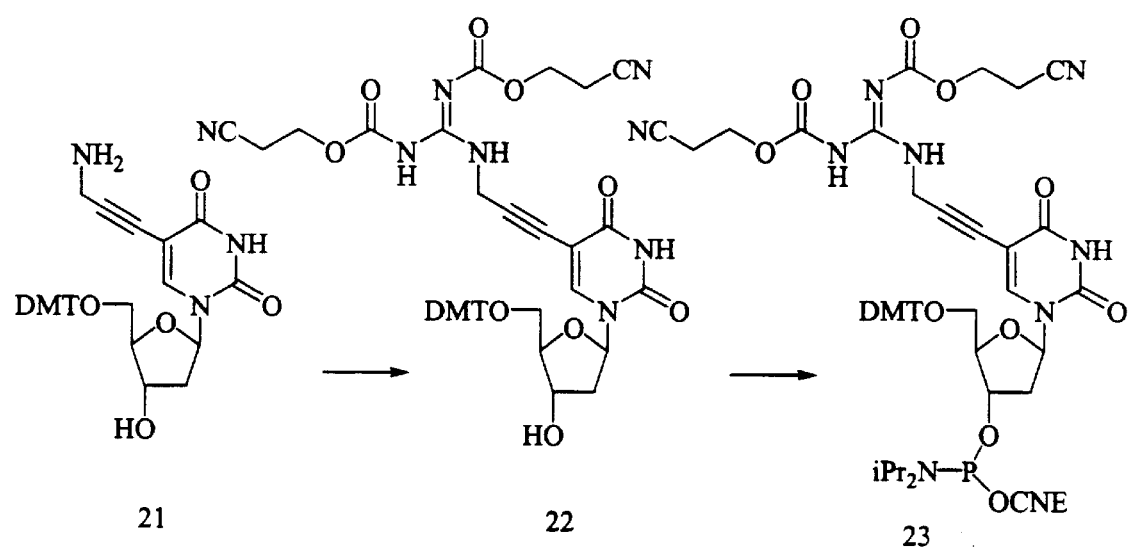
FIG. 11 shows the synthesis of compounds 22–23.
Figure 12:
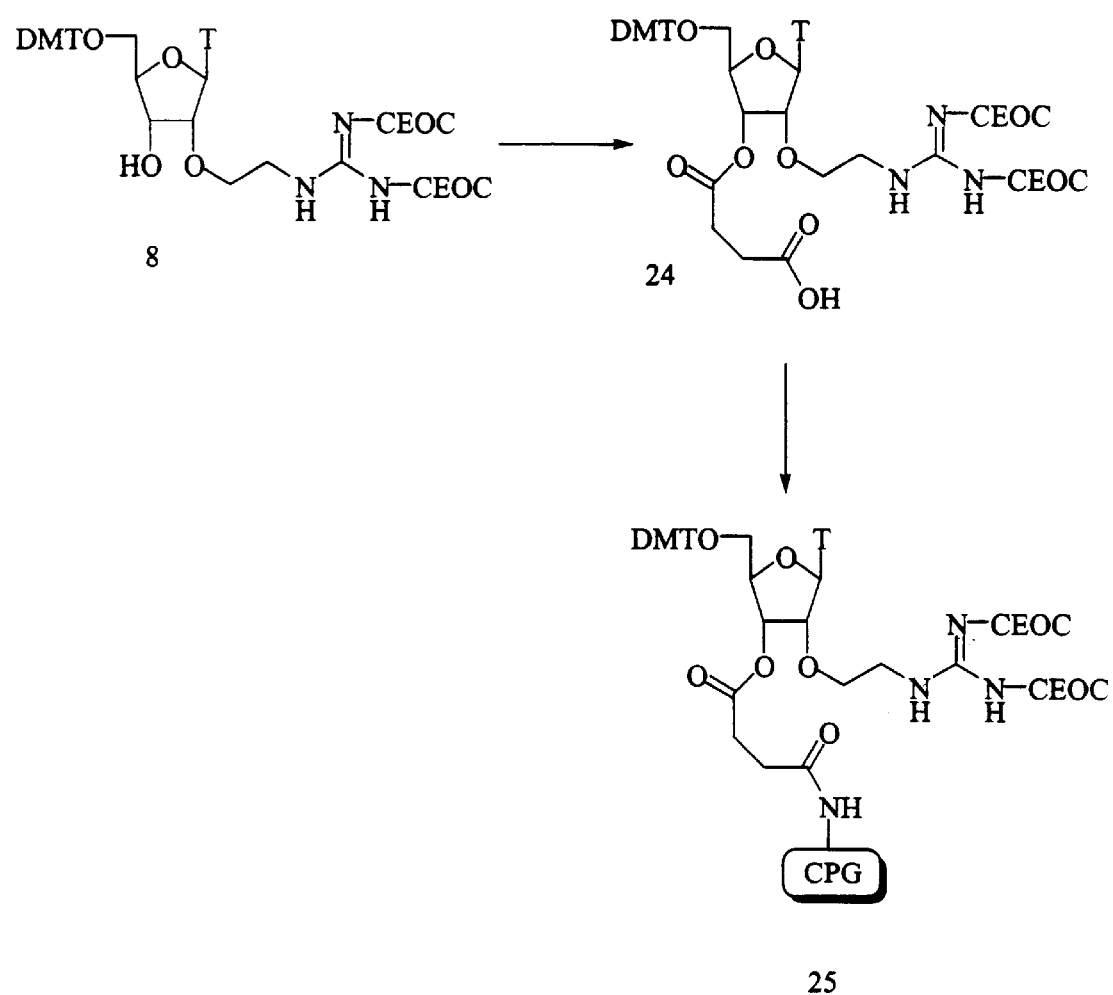
FIG. 12 shows the synthesis of compounds 24–25.
Figure 13:
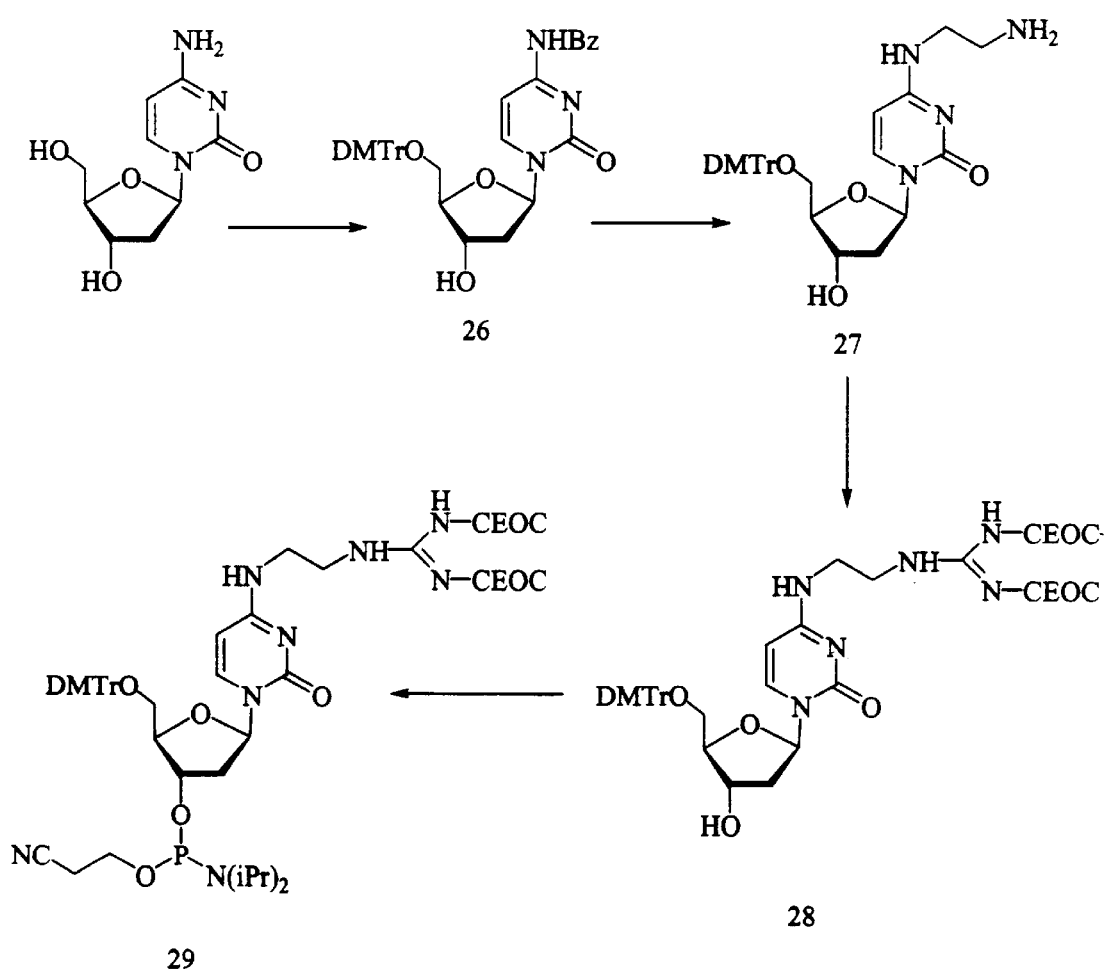
FIG. 13 shows the synthesis of compounds 26–29.
Figure 14:
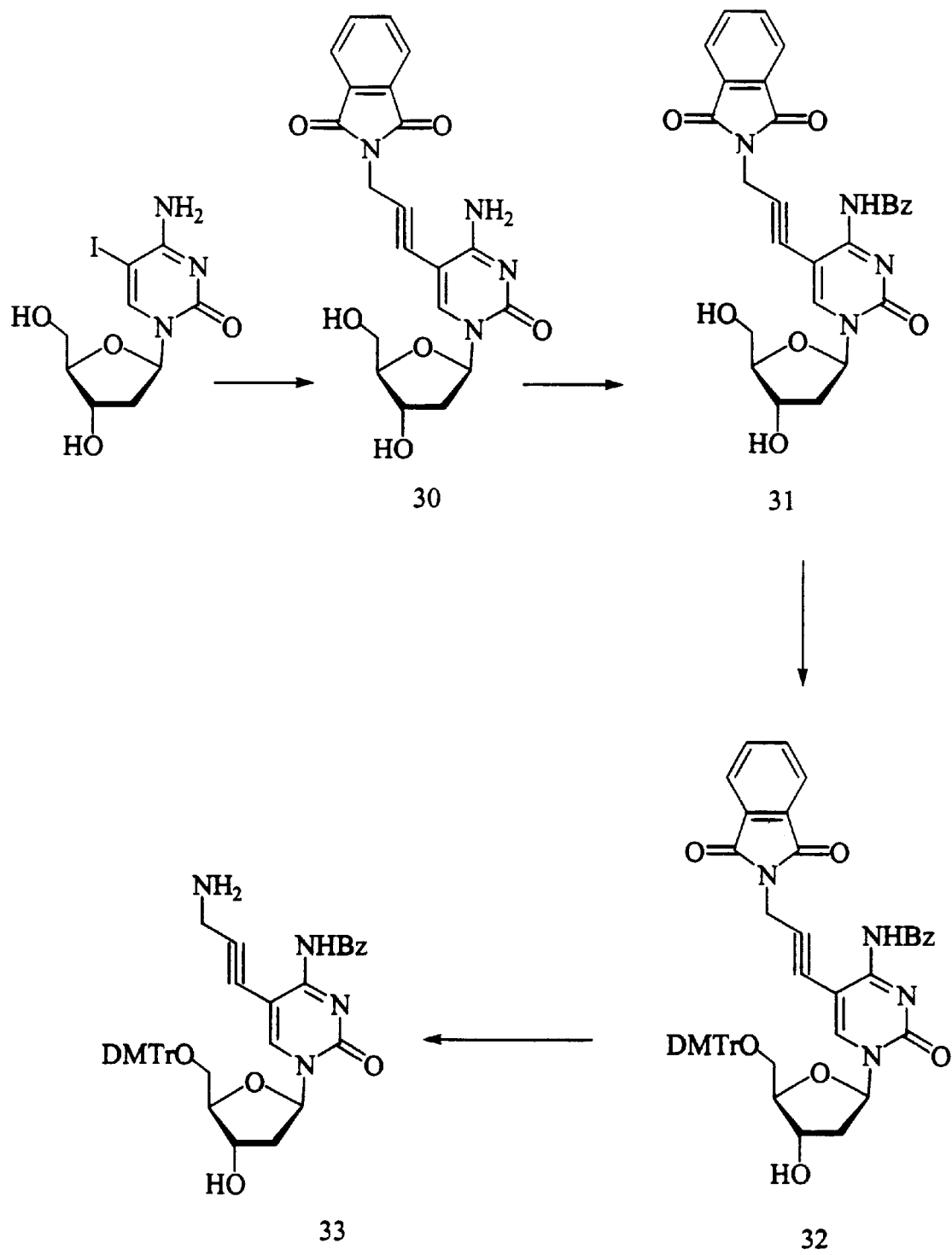
FIG. 14 shows the synthesis of compounds 30–33.
Figure 15:
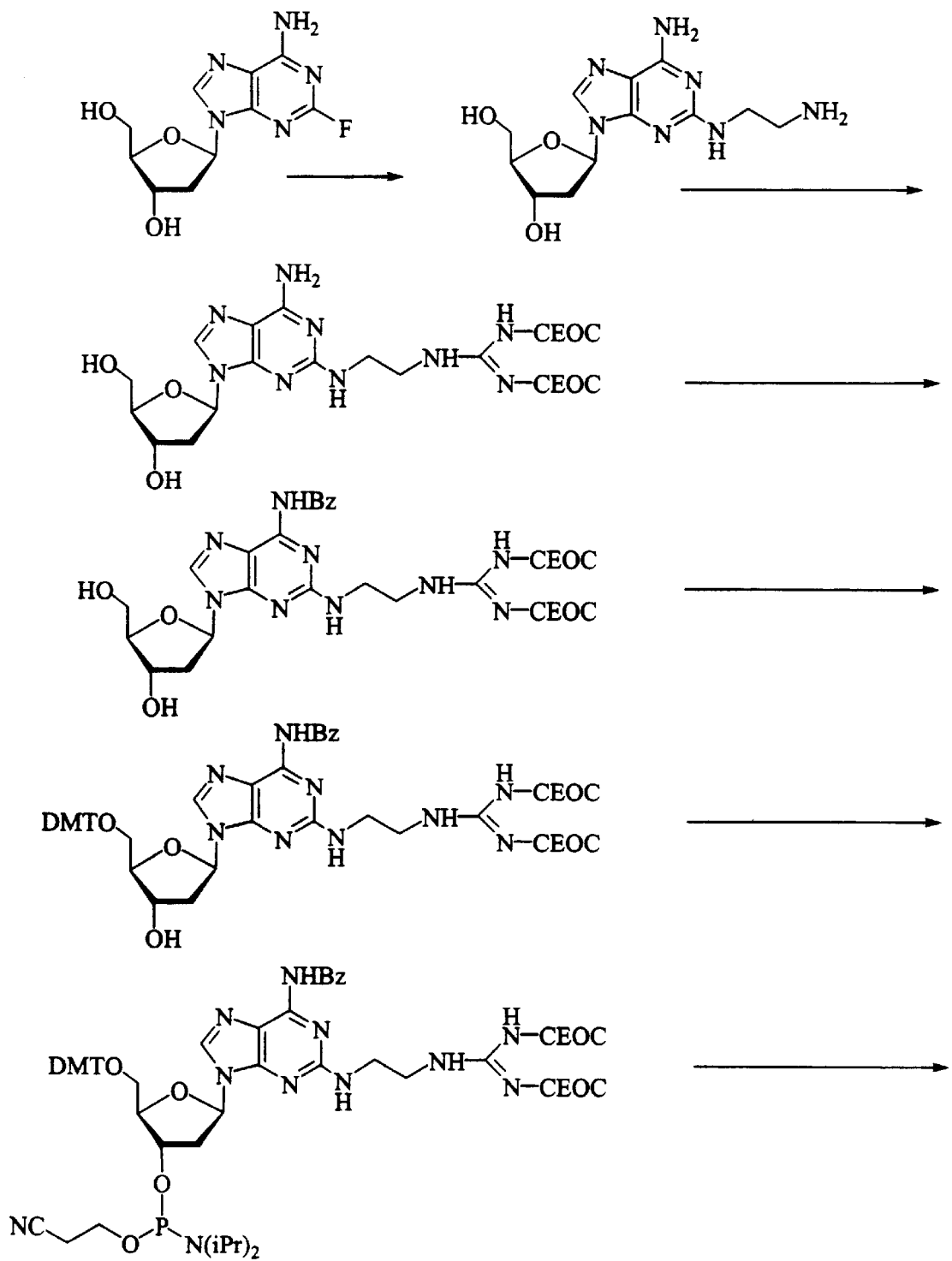
FIG. 15 shows the synthesis of compound 34.
Figure 16:
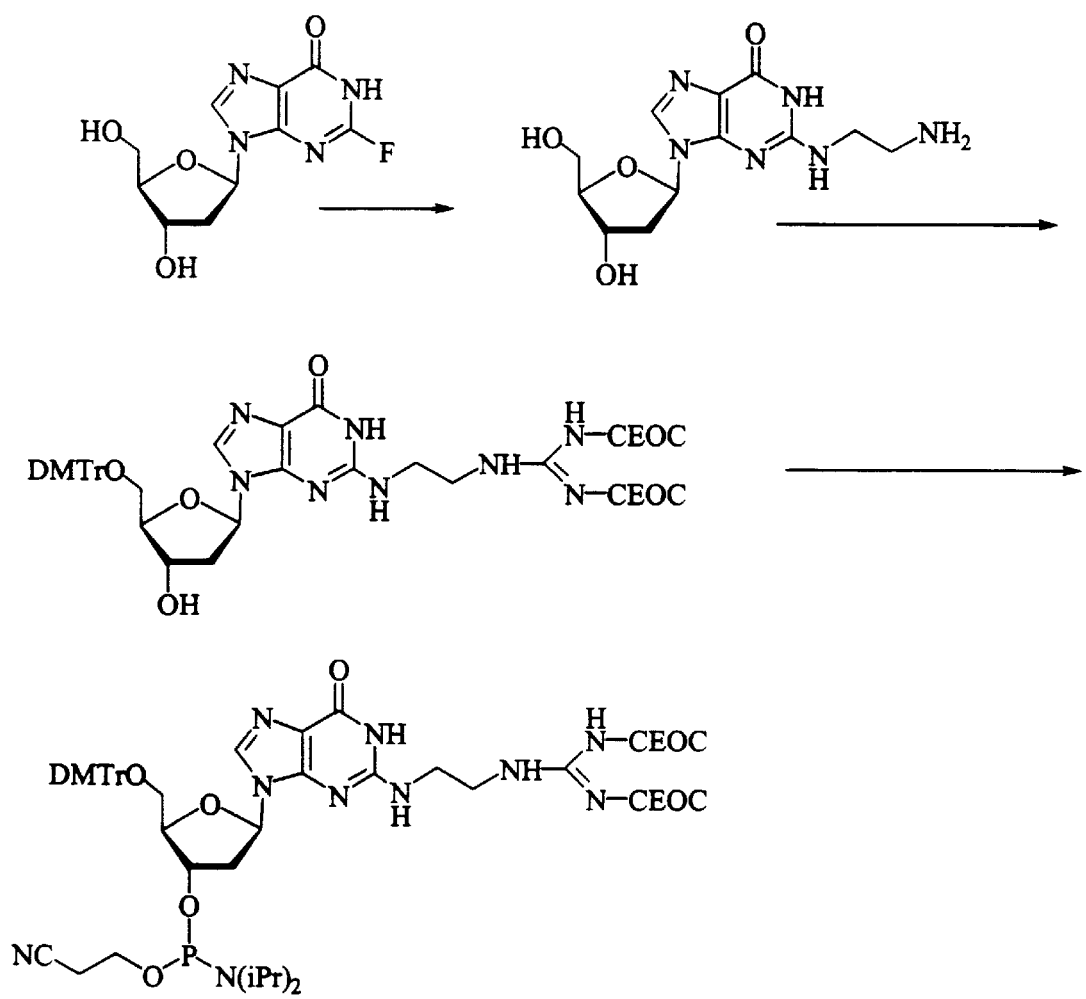
FIG. 16 shows the synthesis of compound 35.
Figure 17:
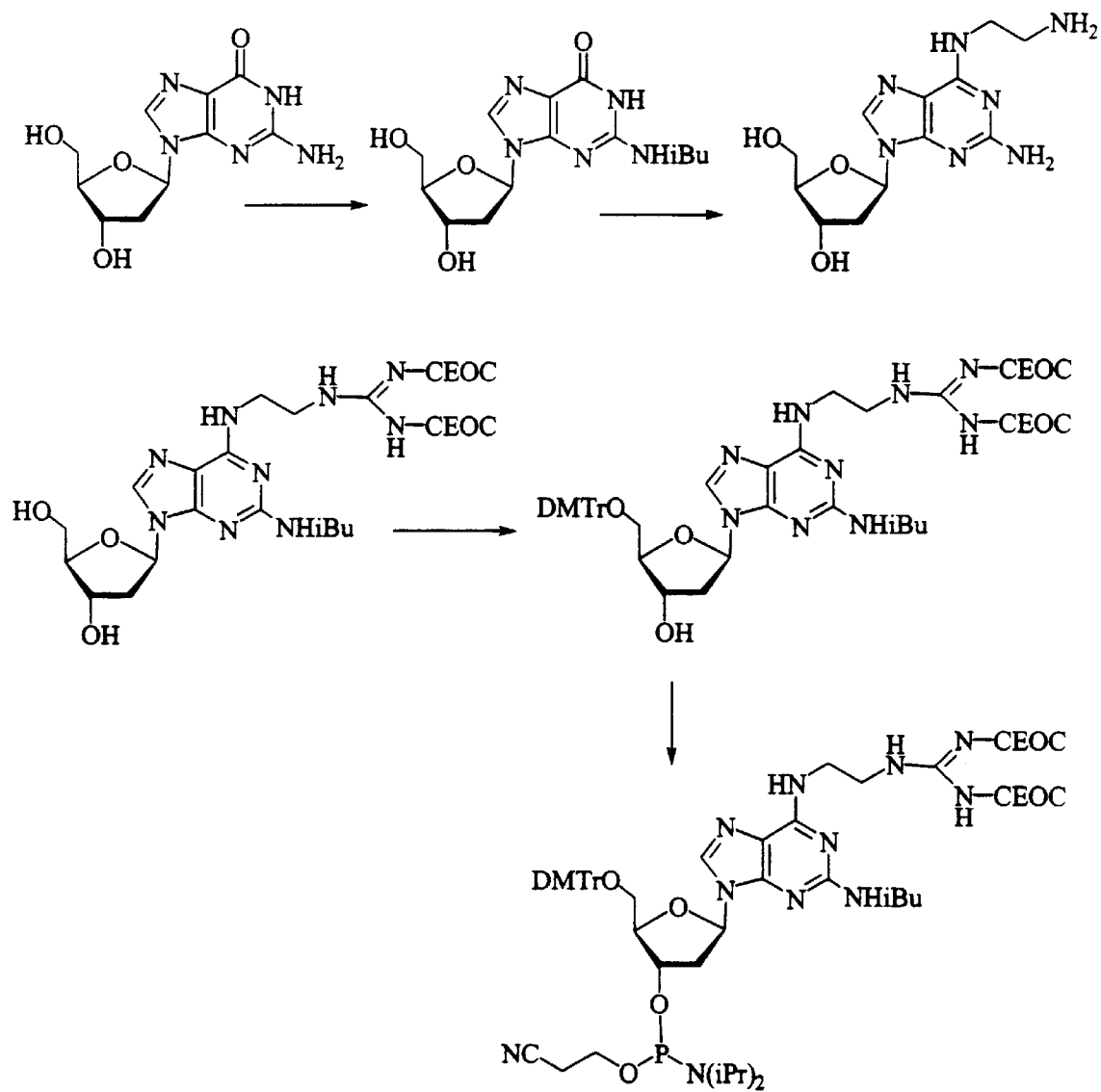
FIG. 17 shows the synthesis of compound 36.
Figure 18:
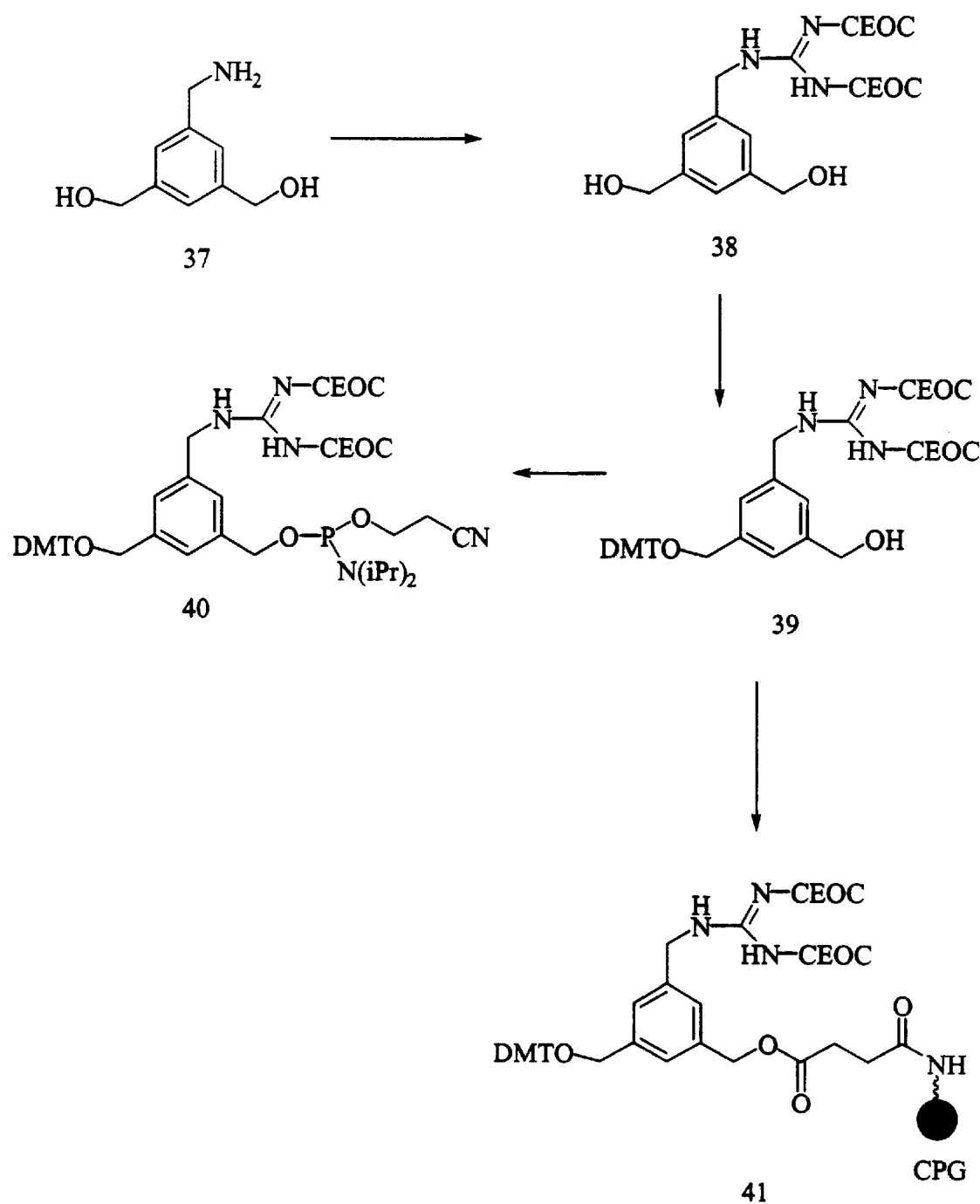
FIG. 18 shows the synthesis of compounds 40 and 41.
Figure 19:
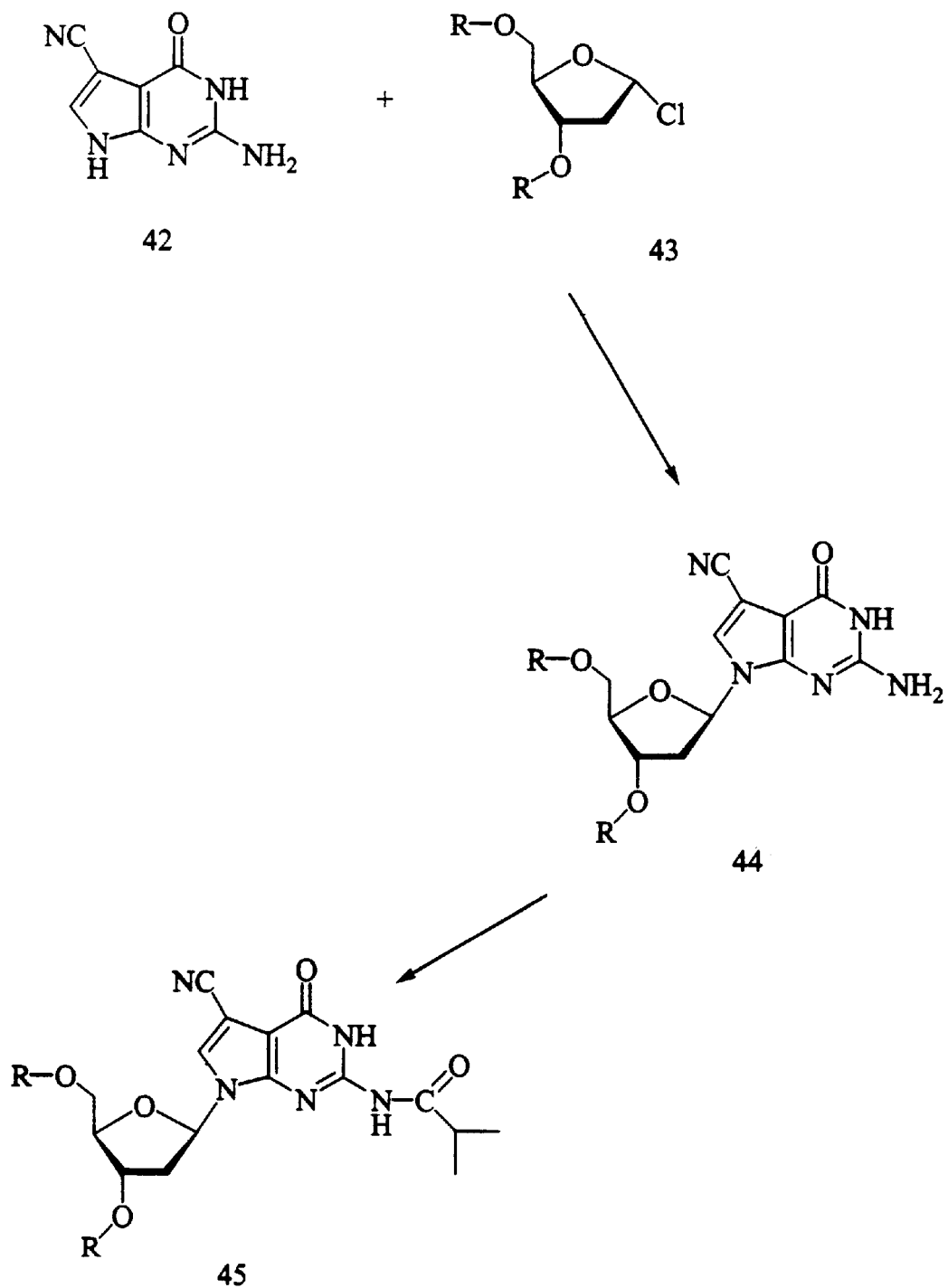
FIG. 19 shows the synthesis of compound 45.
Figure 20:
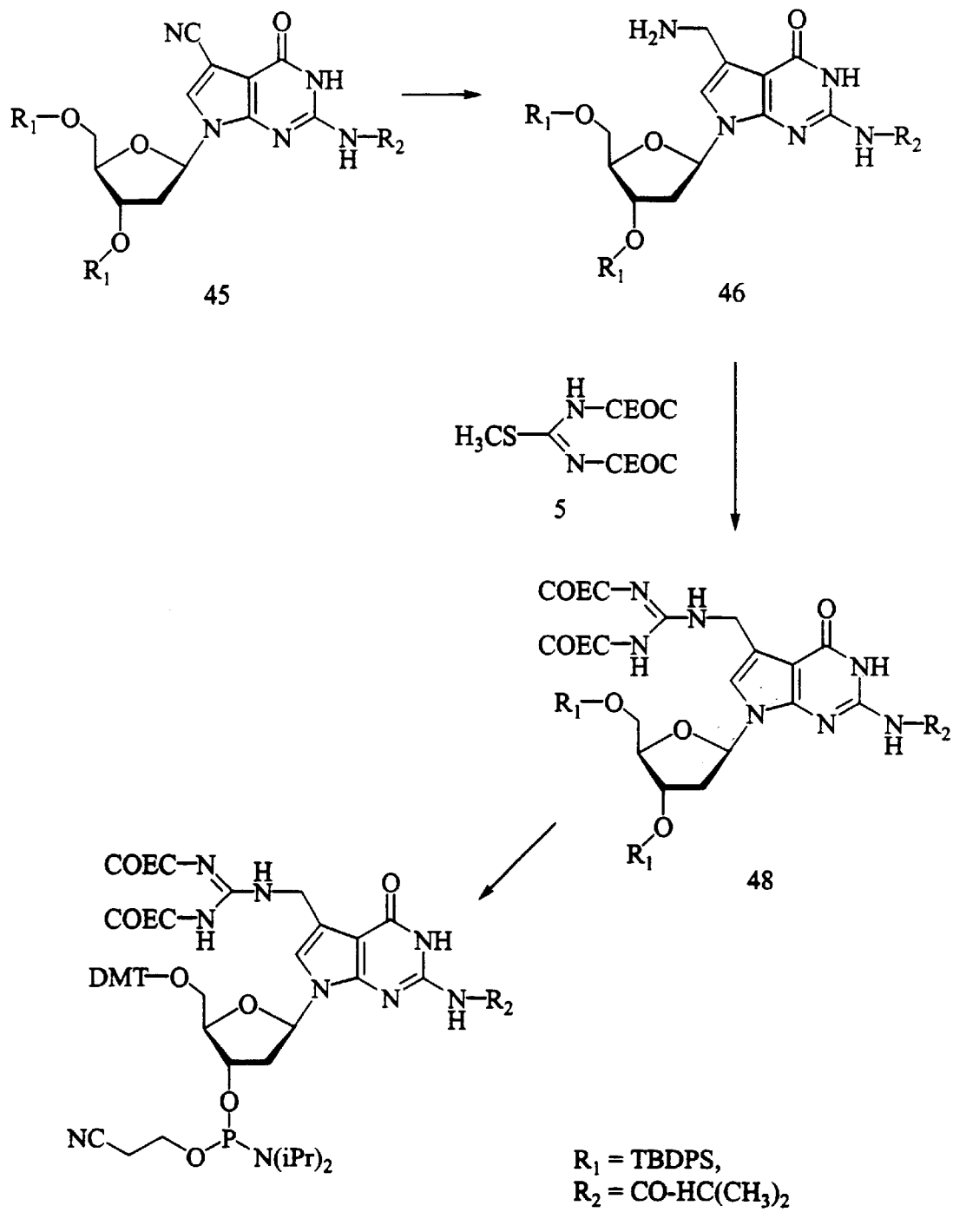
FIG. 20 shows the synthesis of compound 49.
Figure 21:
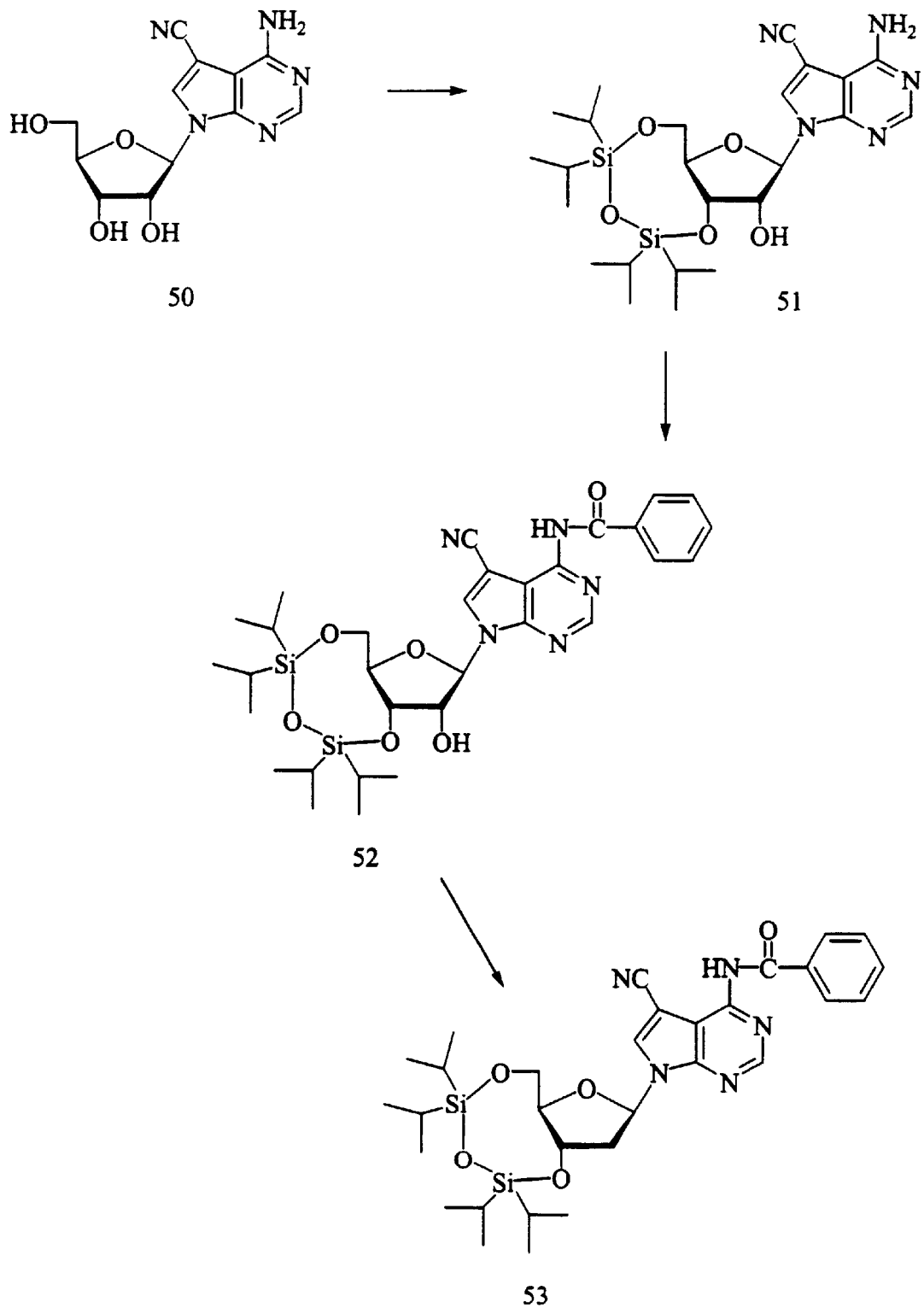
FIG. 21 shows the synthesis of compound 53.
Figure 22:
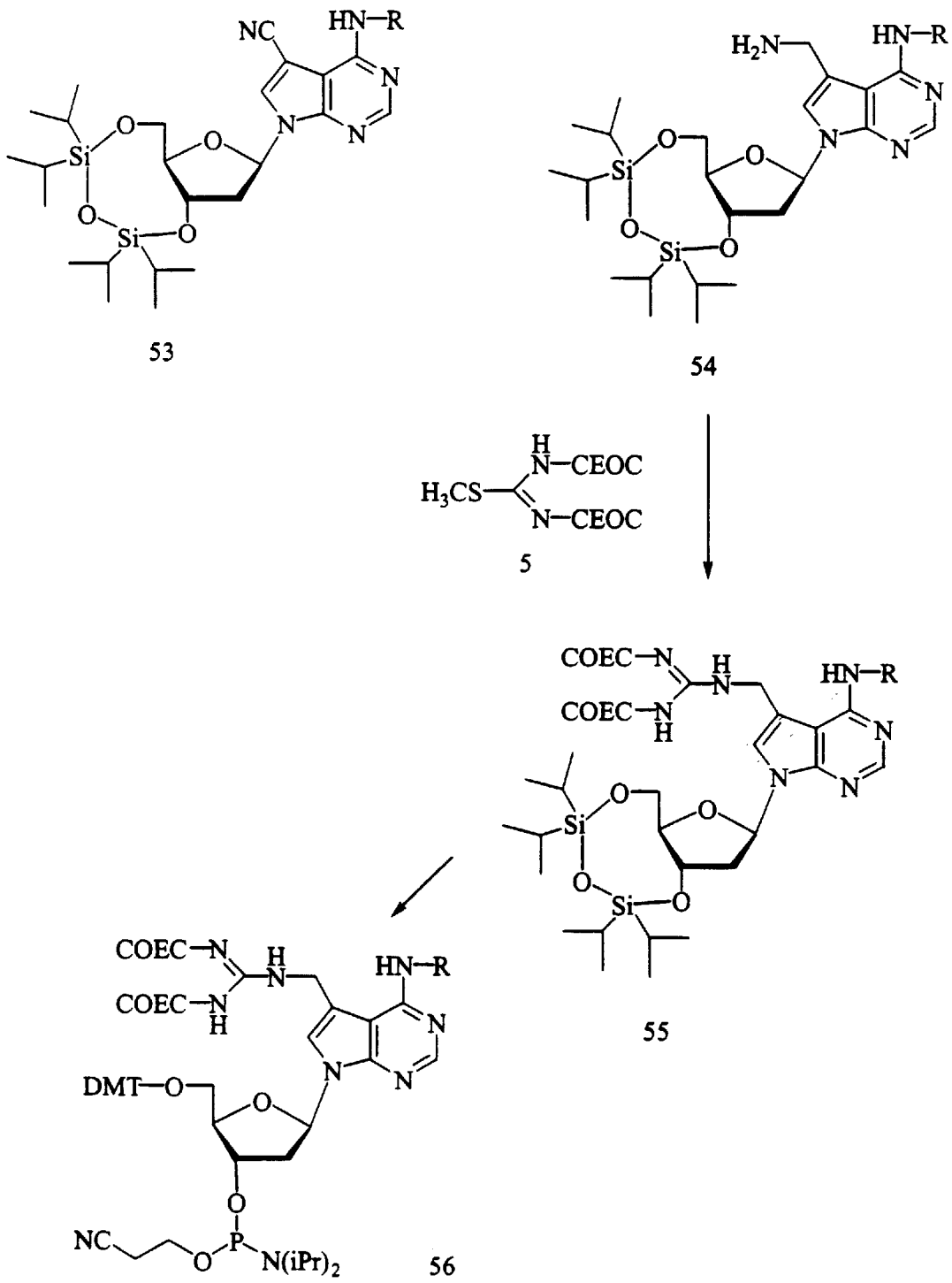
FIG. 22 shows the synthesis of compound 56.

The stability of the oligomers was tested by incubating them with snake venom phosphodiesterase (Phosphodiesterase I, USB # 20240), a non-sequence specific 3'-exonuclease. Typical Nuclease digestion:

70 uL nanopure water
10 uL 1 uM $^{32}$P labeled oligonucleotide
10 uL 10× buffer
10 uL SVPD @ 5×10$^{-2}$ Units/mL
100 uL Final reaction conditions:
Buffer
  50 mM Tris.HCl, pH 8.0
  75 mM NaCl
  14 mM MgCl$_2$
Oligomer concentration
  100 nM
Enzyme concentration
  5×10$^{-3}$ Units/mL The reactions were incubated at 37° C. Aliquots (5 µL) were removed over a set time course and transferred to tubes containing 2× TBE in formamide with a trace of Bromphenol Blue, then frozen at B4° C. until analysis. The reactions were analyzed by PAGE/Phosphorimaging. Samples at specific time points were centrifuged briefly to settle the samples, then loaded on a 20% acrylamide gel. After running, the gels were exposed and read with a Molecular Dynamics Phosphorimager (FIG. 4). The % full length (N) of oligomer in each lane was calculated.

As shown in FIG. 4, the placement of guanidinium residue protects the oligonucleotide phosphodiester internucleotide linkage against exonuclease degradation. With increasing number of substituents, the nuclease resistance also increases. Placement of four guanidium substituents in a 19mer at the 3'-end fully protects the oligomer.

Example 36

Synthesis of 2'-O-(2-guanidinium)-ethyl Oligonucleotides for Triplex Formation The sequence specific recognition of duplex DNA by pyrimidine oligonucleotides involves the formation of triple helical structures which are stabilized by Hoogsteen hydrogen bonds between the bases on a DNA target and pyrimidine third strand. (Neidel, *Anti-Cancer Drug Des.* 12, 433–442, 1997; Giovannangeli and Helene, Antisense Nulceic Acid Drug Dev. 7, 413–421, 1997; Maher, *Cancer Invest.* 14, 66–82, 1996.)

Examination of a molecular model of triple helix with a RNA third strand indicates that the 2'-hydroxyl groups of RNA and the phosphate groups of the DNA second strand are in close proximity. (Hélène, et al., *Nucleic Acid Res.* 21, 5547–5553, 1993.) 2'-Aminoethoxy modified oligonucleotides stabilize the triplex formation. (Cuenourd et al., *Angew. Chem. Int. Ed.*, 37, 1288–1291, 1998.) 2'-Guanidinoethyl modified oligonucleotides, by virtue of its stabilized multi-point charge site, would stabilize triplex formation. Following duplex DNA was targeted with 2'-guanidiniumethyl-modified oligonucleotides (SEQ ID No. 04: ISIS 113254, ISIS 113929 and ISIS 113255) used as strand 3 for triplex formation.

```
Strand 2
5'-GCT AAA AAG AGA GAG AGA TCG-3'    SEQ ID No. 05

Strand 1
5'-CGA TTT TTC TCT CTC TCT AGC-5'    SEQ ID No. 06
```

Example 37

Synthesis of Compounds 40 and 41

Compound 37 is synthesized according to the procedure described by Behrens et al. (Bioorg. Med. Chem. Lett., 1995, 5, 1785). Compound 37 is converted to the guanidinium derivative 38 using reagent 5 as described in Example 8. Compound 38 is then treated with 1 equivalent of 4,4'-dimethoxytrityl chloride and pyridine to form compound 39, which is then phosphitylated to yield compound 40. Synthesis of an oligomer using compound 40 results in an oligomer having the guanidinium group at the 5' end.

Also, compound 39 is succinylated and coupled to controlled pore glass (CPG) to yield compound 41. Synthesis of an oligomer using compound 41 results in an oligomer having the guanidinium group at the 3' end.

Example 38

Synthesis of Compounds 49 and 56

(FIGS. 19–23)

Compound 42 is synthesized according to the reported procedures (see Migawa et al., *Synthetic Communications*, 1996, 26, 3317–3322). Glycosylation of 42 with chloro sugar 43 according to a previously reported procedure (Ramasamy et al., *Chem. Soc. Perkin Trans.*, I, 1989, 2375–2384) gives nucleoside 44 which is then acylated at the $N^2$ position to give the completely protected nucleoside 45. Compound 45 is then reduced to the 7-aminomethyl derivative 46 in the presence of palladium and hydrogen gas at 50 psi. Guanylation of 46 with guanylating reagent 5 in DMF and triethyl amine gives 48 which is then subject to desilylation, selective tritylation at the 5' position and phosphitylation at the 3' position to give compound 49.

Compound 50 (prepared as per the procedure of: Porcari et al., *Nucleosides and Nucleotides*, 1999, 18, 153–159) is silylated with Markovick reagent in pyridine to give Compound 51. Compound 51 is then acylated at the 4-position of the exocyclic amino group with benzyl chloride and pyridine to give the bisbenzoyl derivative which is converted to mono benzoyl derivitive, compound 52, by treatment with aqueous ammonia. Deoxygenation of 52 at the 2' position gives compound 53. Catalytic hydrogenation of 53 in the presence of Palladium and hydrogen gives compound 54 which is converted into the guanidino derivative 55 according to the procedure used for 5. Compound 55 on desilylation, tritylation at 5'-position and phosphitylation at 3'-position gives compound 56.

Example 39

TABLE III

Triplex binding affinity enhancement of 2'-O-GE modification against double stranded DNA

| T* | II TM ° C. | II ΔTm/mod/° C. | III TM ° C. | III ΔTm/mod/° C. | IV TM ° C. | IV ΔTm/mod/° C. |
|---|---|---|---|---|---|---|
| 2'-deoxy | | | | | 21.9 | |
| 2'-O-AE | | | | | 35.9 | 3.5 |
| 2'-O-AP* | | | | | 32.4 | 2.1 |
| 2'-O-GE | 29.3 | 2.53 | 32.4 | 2.65 | 43.6 | 4.12 |

Oligomers II, III and IV each have SEQ ID NO. 4 (TTT TTC TCT CTC TCT) with various groups attached at various 2'-positions ((2'-H, 2'-O-aminoethyl (2'-O-AE); 2'-aminopropyl (2'-O-AP); and 2'-guanidiniumethyl (2'-O-GE)). Oligomer II is modified at the 1,3 and 5 positions (SEQ ID NO. 14–17 T*TT* TT*C TCT CTC TCT); oligomer III is modified at the 2, 5, 9 and 12 positions (SEQ ID NO. 18–21 TT*T TT*C TCT* CTC T*CT); and oligomer IV is modified at the 1–5 positions (SEQ ID NO. 22–25 T*T*T* T*T*C TCT CTC TCT).

The results of the study show that the 2'-O-GE modification has imparts higher binding affinity to the resulting modified oligomers.

What is claimed is:

1. A monomer of the formula:

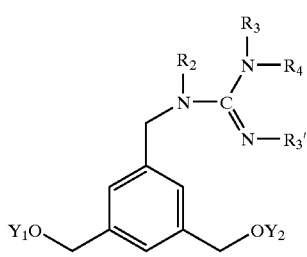

wherein:

$Y_1$ is a hydroxyl protecting group;

$Y_2$ is a phosphoramidite, H-phosphonate, phosphate triester, or a linking moiety attached to a solid support;

each $R_2$, $R_3$, $R_{3'}$, and $R_4$ is, independently, hydrogen, $C(O)R_5$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, or arylsulfonyl, wherein the substituent groups are selected from hydroxyl, amino, alkoxy, carboxy, benzyl, phenyl, nitro, thiol, thioalkoxy, halogen, alkyl, aryl, alkenyl and alkynyl;

or $R_3$ and $R_4$, together, are $R_7$;

each $R_5$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl; iso-butyryl, phenyl or aryl;

$R_7$ is hydrogen or forms a phthalimide moiety with the nitrogen atom to which it is attached; and n is an integer from 1 to about 6.

2. The compound of claim 1 wherein $Y_1$ is dimethoxytrityl.

3. The compound of claim 1 wherein $Y_1$ is monomethoxytrityl.

4. The compound of claim 1 wherein $Y_2$ is a linking moiety attached to a solid support.

5. The compound of claim 1 wherein $Y_2$ is succinyl controlled pore glass (CPG).

* * * * *

SEQUENCE LISTING

<160> NUMBER OF SEQ ID NOS: 25

<210> SEQ ID NO 1
<211> LENGTH: 16
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: T*=2'-O-[2-(guanidinium)ethyl]
<220> FEATURE:
<221> NAME/KEY: misc_feature
<222> LOCATION: (7)..(7)
<223> OTHER INFORMATION: T*=2'-O-[2-(guanidinium)ethyl]
<220> FEATURE:
<221> NAME/KEY: misc_feature
<222> LOCATION: (9)..(9)
<223> OTHER INFORMATION: T*=2'-O-[2-(guanidinium)ethyl]
<220> FEATURE:
<221> NAME/KEY: misc_feature
<222> LOCATION: (15)..(15)
<223> OTHER INFORMATION: T*=2'-O-[2-(guanidinium)ethyl]

<400> SEQUENCE: 1
tccaggtgtc cgcatc                                                  16

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (8)..(11)
<223> OTHER INFORMATION: T*=2'-O-[2-(guanidinium)ethyl]

<400> SEQUENCE: 2
ctcgtacttt tccggtcc                                                18

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (16)..(19)
<223> OTHER INFORMATION: T*=2'-O-[2-(guanidinium)ethyl]

<400> SEQUENCE: 3
tttttttttt tttttttt                                                19

<210> SEQ ID NO 4
<211> LENGTH: 15
<212> TYPE: DNA
<213> ORGANISM: Artificial Sequence
<220> FEATURE:
<223> OTHER INFORMATION: Oligonucleotide

<400> SEQUENCE: 4
tttttctctc tctct                                                   15

<210> SEQ ID NO 5
<211> LENGTH: 21

```
<212> TYPE: DNA
<213> ORGANISM: Artificial Sequence
<220> FEATURE:
<223> OTHER INFORMATION: Oligonucleotide

<400> SEQUENCE: 5
gctaaaaaga gagagagatc g                                              21

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6 cgattttttct ctctctctag c                                             21

<210> SEQ ID NO 7
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: T*=2'-O-[2-(guanidinium)ethyl]

<400> SEQUENCE: 7
tttttttttt ttttttttt                                                 19

<210> SEQ ID NO 8
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: T*=2'-O-[2-(guanidinium)ethyl]

<400> SEQUENCE: 8
tttttctctc tctct                                                     15

<210> SEQ ID NO 9
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: T*=2'-O-[2-(guanidinium)ethyl]
<220> FEATURE:
<221> NAME/KEY: misc_feature
<222> LOCATION: (5)..(5)
<223> OTHER INFORMATION: T*=2'-O-[2-(guanidinium)ethyl]
<220> FEATURE:
<221> NAME/KEY: misc_feature
<222> LOCATION: (9)..(9)
<223> OTHER INFORMATION: T*=2'-O-[2-(guanidinium)ethyl]
<220> FEATURE:
<221> NAME/KEY: misc_feature
<222> LOCATION: (13)..(13)
<223> OTHER INFORMATION: T*=2'-O-[2-(guanidinium)ethyl]

<400> SEQUENCE: 9
```
tttttctctc tctct                                                  15

<210> SEQ ID NO 10
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: T*=2'-O-[2-(guanidinium)ethyl]
<220> FEATURE:
<221> NAME/KEY: misc_feature
<222> LOCATION: (3)..(3)
<223> OTHER INFORMATION: T*=2'-O-[2-(guanidinium)ethyl]
<220> FEATURE:
<221> NAME/KEY: misc_feature
<222> LOCATION: (5)..(5)
<223> OTHER INFORMATION: T*=2'-O-[2-(guanidinium)ethyl]

<400> SEQUENCE: 10
tttttctctc tctct                                                  15

<210> SEQ ID NO 11
<211> LENGTH: 16
<212> TYPE: DNA
<213> ORGANISM: Artificial Sequence
<220> FEATURE:
<223> OTHER INFORMATION: Oligonucleotide

<400> SEQUENCE: 11
tccaggtgtc cgcatc                                                 16

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide

<400> SEQUENCE: 12
ctcgtacttt tccggtcc                                               18

<210> SEQ ID NO 13
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (17)..(17)
<223> OTHER INFORMATION: T*=2'-O-[2-(guanidinium)ethyl]
<220> FEATURE:
<221> NAME/KEY: misc_feature
<222> LOCATION: (19)..(19)
<223> OTHER INFORMATION: T*=2'-O-[2-(guanidinium)ethyl]

<400> SEQUENCE: 13
tttttttttt tttttttt                                               19

<210> SEQ ID NO 14
<211> LENGTH: 15
<212> TYPE: DNA
<213> ORGANISM: Artificial Sequence
<220> FEATURE:
<223> OTHER INFORMATION: Oligonicleotide
<220> FEATURE:
<221> NAME/KEY: misc_feature

```
<222> LOCATION: (1)..(1)
<223> OTHER INFORMATION: T*=2'-deoxy
<220> FEATURE:
<221> NAME/KEY: misc_feature
<222> LOCATION: (3)..(3)
<223> OTHER INFORMATION: T*=2'-deoxy
<220> FEATURE:
<221> NAME/KEY: misc_feature
<222> LOCATION: (5)..(5)
<223> OTHER INFORMATION: T*=2'-deoxy

<400> SEQUENCE: 14
tttttctctc tctct                                          15

<210> SEQ ID NO 15
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: T*=2'-O-AE
<220> FEATURE:
<221> NAME/KEY: misc_feature
<222> LOCATION: (3)..(3)
<223> OTHER INFORMATION: T*=2'-O-AE
<220> FEATURE:
<221> NAME/KEY: misc_feature
<222> LOCATION: (5)..(5)
<223> OTHER INFORMATION: T*=2'-O-AE

<400> SEQUENCE: 15
tttttctctc tctct                                          15

<210> SEQ ID NO 16
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: T*=2'-O-AP*
<220> FEATURE:
<221> NAME/KEY: misc_feature
<222> LOCATION: (3)..(3)
<223> OTHER INFORMATION: T*=2'-O-AP*
<220> FEATURE:
<221> NAME/KEY: misc_feature
<222> LOCATION: (5)..(5)
<223> OTHER INFORMATION: T*=2'-O-AP*

<400> SEQUENCE: 16
tttttctctc tctct                                          15

<210> SEQ ID NO 17
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: T*=2'-O-GE
<220> FEATURE:
<221> NAME/KEY: misc_feature
<222> LOCATION: (3)..(3)
<223> OTHER INFORMATION: T*=2'-O-GE
<220> FEATURE:
```

```
<221> NAME/KEY: misc_feature
<222> LOCATION: (5)..(5)
<223> OTHER INFORMATION: T*=2'-O-GE

<400> SEQUENCE: 17 ttttctctc tctct                                                              15

<210> SEQ ID NO 18
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: T*=2'-deoxy
<220> FEATURE:
<221> NAME/KEY: misc_feature
<222> LOCATION: (5)..(5)
<223> OTHER INFORMATION: T*=2'-deoxy
<220> FEATURE:
<221> NAME/KEY: misc_feature
<222> LOCATION: (9)..(9)
<223> OTHER INFORMATION: T*=2'-deoxy
<220> FEATURE:
<221> NAME/KEY: misc_feature
<222> LOCATION: (13)..(13)
<223> OTHER INFORMATION: T*=2'-deoxy

<400> SEQUENCE: 18 ttttctctc tctct                                                              15

<210> SEQ ID NO 19
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: T*=2'-O-AE
<220> FEATURE:
<221> NAME/KEY: misc_feature
<222> LOCATION: (5)..(5)
<223> OTHER INFORMATION: T*=2'-O-AE
<220> FEATURE:
<221> NAME/KEY: misc_feature
<222> LOCATION: (9)..(9)
<223> OTHER INFORMATION: T*=2'-O-AE
<220> FEATURE:
<221> NAME/KEY: misc_feature
<222> LOCATION: (13)..(13)
<223> OTHER INFORMATION: T*=2'-O-AE

<400> SEQUENCE: 19 ttttctctc tctct                                                              15

<210> SEQ ID NO 20
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: T*=2'-O-AP*
<220> FEATURE:
<221> NAME/KEY: misc_feature
<222> LOCATION: (5)..(5)
<223> OTHER INFORMATION: T*=2'-O-AP*
```

```
<220> FEATURE:
<221> NAME/KEY: misc_feature
<222> LOCATION: (9)..(9)
<223> OTHER INFORMATION: T*=2'-O-AP*
<220> FEATURE:
<221> NAME/KEY: misc_feature
<222> LOCATION: (13)..(13)
<223> OTHER INFORMATION: T*=2'-O-AP*

<400> SEQUENCE: 20
tttttctctc tctct                                                        15

<210> SEQ ID NO 21
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: T*=2'-O-GE
<220> FEATURE:
<221> NAME/KEY: misc_feature
<222> LOCATION: (5)..(5)
<223> OTHER INFORMATION: T*=2'-O-GE
<220> FEATURE:
<221> NAME/KEY: misc_feature
<222> LOCATION: (9)..(9)
<223> OTHER INFORMATION: T*=2'-O-GE
<220> FEATURE:
<221> NAME/KEY: misc_feature
<222> LOCATION: (13)..(13)
<223> OTHER INFORMATION: T*=2'-O-GE

<400> SEQUENCE: 21
tttttctctc tctct                                                        15

<210> SEQ ID NO 22
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: T*=2'-deoxy

<400> SEQUENCE: 22
tttttctctc tctct                                                        15

<210> SEQ ID NO 23
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: T*=2'-O-AE

<400> SEQUENCE: 23
tttttctctc tctct                                                        15

<210> SEQ ID NO 24
<211> LENGTH: 15
<212> TYPE: DNA
<213> ORGANISM: Artificial Sequence
<220> FEATURE:
```

```
<223> OTHER INFORMATION: Oligonucleotide
<220> FEATURE:
<221> NAME/KEY: misc_feature
<222> LOCATION: (1)..(5)
<223> OTHER INFORMATION: T*=2'-O-AP*

<400> SEQUENCE: 24
tttttctctc tctct                                            15

<210> SEQ ID NO 25
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: T*=2'-O-GE

<400> SEQUENCE: 25
tttttctctc tctct                                            15
```